(12) United States Patent
Berndt

(10) Patent No.: US 8,600,142 B2
(45) Date of Patent: Dec. 3, 2013

(54) METHOD AND APPARATUS FOR AUTOMATED STAINING OF BIOLOGICAL MATERIALS

(75) Inventor: Klaus W. Berndt, Cockeysville, MD (US)

(73) Assignee: Beckton, Dickinson and Company, Franklin Lakes, NJ (US)

( * ) Notice: Subject to any disclaimer, the term of this patent is extended or adjusted under 35 U.S.C. 154(b) by 804 days.

(21) Appl. No.: 12/529,065

(22) PCT Filed: Feb. 29, 2008

(86) PCT No.: PCT/US2008/055471
§ 371 (c)(1),
(2), (4) Date: Jun. 3, 2010

(87) PCT Pub. No.: WO2008/109422
PCT Pub. Date: Sep. 12, 2008

(65) Prior Publication Data
US 2010/0240021 A1 Sep. 23, 2010

Related U.S. Application Data

(60) Provisional application No. 60/892,736, filed on Mar. 2, 2007.

(51) Int. Cl.
*G06K 9/00* (2006.01)
(52) U.S. Cl.
USPC .......................................... 382/133; 382/128
(58) Field of Classification Search
USPC ................................ 382/128, 133; 422/43, 63
See application file for complete search history.

(56) References Cited

U.S. PATENT DOCUMENTS 3,352,280 A 11/1967 Hughes et al.
4,029,470 A 6/1977 Wilkins et al.
(Continued)

FOREIGN PATENT DOCUMENTS

EP 1 508 369 A2 2/2005
JP 08-145871 6/1996
(Continued)

OTHER PUBLICATIONS

International Search Report from International Patent Application No. PCT/US2008/055471, filed Feb. 29, 2008.
(Continued)

*Primary Examiner* — Michelle Le
(74) *Attorney, Agent, or Firm* — Alston & Bird LLP

(57) ABSTRACT

Various embodiments of the present invention provide methods and systems for optimally staining biological samples for analysis. In one embodiment, images of a sample are recorded before and after the application of a staining reagent and a decolorization reagent. A difference image is then generated based at least in part on a comparison of the images of the sample recorded before and after the application of the staining and decolorization reagents. Application parameters of the staining and decolorization reagents are then corrected based at least in part on the difference image such that the reagents may be optimally reapplied to generate a final image of the sample that may enable a user to better differentiate at least one target of interest in the sample. In one example, embodiments of the present invention allow for the generation of images that show only Gram-positive bacteria or only Gram-negative bacteria.

27 Claims, 17 Drawing Sheets

(56) References Cited

U.S. PATENT DOCUMENTS

| | | | |
|---|---|---|---|
| 5,352,613 | A | 10/1994 | Tafas et al. |
| 6,403,367 | B1 | 6/2002 | Cheng et al. |
| 6,468,764 | B1* | 10/2002 | Gibbs et al. .................. 435/40.5 |
| 2003/0081209 | A1 | 5/2003 | Takahashi et al. |
| 2004/0009098 | A1* | 1/2004 | Torre-Bueno ................... 422/63 |
| 2004/0249274 | A1 | 12/2004 | Yaroslavsky et al. |
| 2005/0260698 | A1 | 11/2005 | Fromherz et al. |

FOREIGN PATENT DOCUMENTS

| | | |
|---|---|---|
| JP | 09-503586 A | 4/1997 |
| JP | 10 215894 A | 8/1998 |
| JP | 2005-055180 | 3/2005 |
| WO | WO 96/30124 A1 | 10/1996 |
| WO | WO 03/039441 | 5/2003 |
| WO | WO 03/106157 A2 | 12/2003 |
| WO | WO 2004/083944 A2 | 9/2004 |

OTHER PUBLICATIONS

Office Action for Japanese Application No. 2009-552807 dated Nov. 22, 2012.

Extended Search Report for European Application No. 131517 dated Aug. 6, 2013.

Extended Search Report for European Application No. 131314 dated Aug. 7, 2013.

* cited by examiner

METHOD AND APPARATUS FOR AUTOMATED STAINING OF BIOLOGICAL MATERIALS

CROSS REFERENCE TO RELATED APPLICATIONS

This application is a national stage application filed under 35 U.S.C. 371 of International Application No. PCT/US2008/055471, filed Feb. 29, 2008, which claims priority from U.S. Provisional Application No. 60/892,736, filed Mar. 2, 2007, each of which is incorporated by reference in its entirety herein.

FIELD OF THE INVENTION

The present invention relates to methods and apparatus for the staining of biological material for the purpose of detecting and identifying disease-causing microorganisms. More particularly, the present invention relates to methods and apparatus for performing automated Gram stains on microscope slides.

BACKGROUND OF THE INVENTION

Gram staining is one of the most frequently performed procedures in modern microbiology laboratories. Such procedures are used to broadly classify bacteria as "Gram-positive" or "Gram-negative." After affixing a bacteria-containing sample to a microscope slide, the sample is treated using staining reagents such as crystal violet in combination with Gram's iodine. This first step stains all bacteria a deep blue or violet. The principal difference between "Gram-positive" and "Gram-negative" bacteria is that in "Gram-positive" samples, the staining reagents are absorbed within the whole cellular structure, while in the "Gram-negative" samples, staining occurs only superficially. Consequently, when the sample is subsequently treated with a decolorizing agent (such as acid alcohol), Gram-negative bacteria tend to lose their color, while Gram-positive bacteria remain stained blue or violet.

Gram stains are conventionally prepared and analyzed manually. Manual Gram staining is labor-intensive, requires skilled personnel, and may fail to achieve optimum staining characteristics in the sample set. Non-optimum staining may result in false Gram-positives as well as false Gram-negatives.

There have been different attempts to automate the Gram staining procedure. See, for example, U.S. Pat. No. 4,029,470 to Wilkins et al. ("Wilkins"). Similarly, the Aerospray Slide Stainer, available commercially from Wescor, Inc. of Logan, Utah is a rudimentary automated staining apparatus. Other staining devices include the Midas III Slide Stainer, commercially available from Merck KGaA of Darmstadt, Germany; the Poly Stainer, which is commercially available from IUL Instruments GmbH of Koenigswinter, Germany; and the Automated Gram Stainer, commercially available from the GG&B Company of Wichita Falls, Tex. and described generally in U.S. Pat. No. 6,468,764 to Gibbs et al. None of these instruments or techniques, however, allow for the capability of applying staining and/or decolorizing agents before, during, and/or after examination and/or image processing of a sample slide.

Consequently, there exists a need for an improved automated staining method and system.

SUMMARY OF THE INVENTION

The present invention, in various embodiments, provides a method and system that overcomes many technical problems with regard to the optimization of staining procedures (such as Gram staining, for example) for biological samples. Specifically in one embodiment, the invention provides a method for staining a sample, comprising steps for operably engaging a sample with a sample stage of an imaging system, and recording images of the sample using the imaging system before and after an application of a staining reagent and a decolorization reagent to the sample. The method also comprises generating a difference image based at least in part on a comparison of the images of the sample recorded before and after the application of the staining reagent and the decolorization reagent to the sample, and correcting the application of the staining reagent and the decolorization reagent based at least in part on the difference image. The method further comprises reapplying at least one of the staining reagent and the decolorization reagent according to the correcting step and generating a final image of the sample so as to differentiate at least one target of interest in the sample that may be rendered discernible by the reapplying step.

Some embodiments further provide a method for performing a staining procedure for a sample comprising steps for recording a first image of the sample and applying a staining agent to the sample so as to prepare a stained sample comprising a plurality of stained entities. Some method embodiments further comprise steps for washing the sample with a washing solution prior to recording the first image of the sample so as to ensure that each sample is washed to establish a "zero" level of staining prior to recording the first image (which provides a basis for comparison with images recorded of the sample after the application of at least one of the staining agent and the decolorization agent).

The plurality of stained entities may include at least one of a plurality of stained entities and a plurality of superficially stained entities. In some such embodiments, the staining agent may comprise a Gram stain such that the superficially stained entities, if present, comprise a plurality of Gram-negative entities, and such that the stained entities, if present, comprise a plurality of Gram-positive entities. The method may further comprise recording a second image of the stained sample and generating a first difference image by comparing the second image to the first image so as to determine a location of at least one of the stained entities on the surface.

The method may further comprise applying a decolorizing agent to the stained sample so as to prepare a partially decolorized sample wherein at least a portion of the staining reagent is removed from the superficially stained entities, and recording a third image of the partially decolorized sample. The method may also comprise generating a second difference image by comparing the third image to the second image so as to determine a location of at least one of the superficially stained entities on the surface. Finally, the method may also comprise analyzing the second difference image to determine an exposure time during which the decolorizing agent could be applied to the partially decolorized sample to substantially decolorize the superficially stained entities without substantially decolorizing the stained entities.

In some embodiments, the method may further comprise applying the decolorizing agent to the partially decolorized sample for the determined exposure time so as to prepare a substantially decolorized sample wherein the superficially stained entities are substantially decolorized and wherein the stained entities are not substantially decolorized. In some such embodiments, the method may further comprise: (1) recording a fourth image of the substantially decolorized sample; (2) generating a third difference image by comparing the fourth image to the second image, wherein the third difference image depicts the location of at least one of the superficially stained entities on the surface; and (3) generating a fourth difference image by comparing the fourth image to the first image, wherein the fourth difference depicts a location of at least one of the stained entities on the surface. In method embodiments wherein the locations of the stained entities and the superficially stained entities are at least partially discernible in at least one of the third and fourth difference images, the method may further comprise analyzing a morphology of the stained entities and/or the superficially stained entities.

Various embodiments of the present invention may also provide systems for performing an optimized staining procedure for a sample. In one embodiment, the system comprises a flow chamber defining channel in fluid communication with a supply of a staining agent and a supply of a decolorizing agent. Furthermore, in some such embodiments, the flow chamber may comprise a surface configured for operably engaging the sample therewith. The system may also comprise a fluidics system in fluid communication with the flow chamber, the supply of the staining agent, and/or the supply of the decolorizing agent.

According to such system embodiments, the fluidics system (in cooperation with the flow chamber, for example) may be configured for applying the staining agent to the sample so as to prepare a stained sample comprising a plurality of stained entities, wherein the plurality of stained entities may include at least one of a plurality of stained entities and a plurality of superficially stained entities. As described above with respect to various method embodiments of the present invention, the staining agent may comprise a Gram stain such that the superficially stained entities, if present, comprise a plurality of Gram-negative entities, and such that the stained entities, if present, comprise a plurality of Gram-positive entities. According to various system embodiments, the fluidics system (in cooperation with the flow chamber, for example) may be further configured for applying the decolorizing agent to the stained sample so as to prepare a partially decolorized sample wherein at least a portion of the stain is removed from the superficially stained entities.

In various system embodiments, the flow chamber may be adapted for receiving a slide defining the surface for operably engaging the sample therewith. According to such embodiments, the flow chamber may further comprise a flow channel housing defining a slide aperture configured for receiving the slide such that the sample is disposed substantially between the slide and the flow channel housing when the slide is disposed in the slide aperture. Furthermore, the flow channel housing may comprise a substantially translucent material such that the imaging system is capable of recording images of the sample while the sample is disposed between the slide and the flow channel housing.

The system may also comprise an imaging system disposed adjacent to the flow chamber such that the sample is positioned within a field of view of the imaging system. In such system embodiments, the imaging system may be configured for monitoring an application of at least one of the staining agent and the decolorizing agent via the flow chamber. Furthermore, the imaging system may also be configured for generating a difference image by comparing at least one image of the sample obtained before a first application of the decolorizing agent and at least one image of the sample obtained after the first application of the decolorizing agent. The imaging system may also be configured to be capable of determining an exposure time for a second application of the decolorizing agent based at least in part on the difference image so as to substantially decolorize the superficially stained entities without substantially decolorizing the stained entities such that the stained entities may be more readily discerned from the superficially stained entities.

The system may also comprise, in some embodiments, a controller device in communication with the imaging system and the fluidics system. The controller device may be further configured to control the application of at least one of the staining agent and the decolorizing agent based at least in part on the images and/or difference images generated by the imaging system.

In some system embodiments, the imaging system may comprise a camera device configured to be capable of recording images of the sample while the sample is disposed in the flow chamber (such as between the slide and the flow channel housing, for example). According to some such embodiments, the imaging system may also comprise an actuator device operably engaged with the camera device and configured for adjusting a position of the camera device relative to the flow chamber. Furthermore, in some system embodiments, the imaging system may also comprise an image processing computer configured for generating the difference image. In some such embodiments, the image processing computer may be configured for generating the difference image using processes that may include, but are not limited to: image subtraction; image addition; image ratio calculation; and combinations of such processes.

As described generally herein with respect to various method embodiments, the imaging system may be configured for recording a first image of the sample and subsequently recording a second image of the stained sample after applying the staining agent to the sample using the fluidics system in cooperation with the flow chamber. The imaging system may be further configured for generating a first difference image by comparing the second image to the first image so as to determine a location of at least one of the stained entities (i.e. the "Gram-positive" entities, in some embodiments) on the surface. Furthermore, the imaging system may be further configured for recording a third image of the partially decolorized sample after applying the decolorizing agent using the flow chamber, and subsequently generating a second difference image by comparing the third image to the second image so as to determine a location of at least one of the superficially stained entities (i.e. the "Gram-negative" entities, in some embodiments). The imaging system may be further configured for analyzing the second difference image to determine an exposure time during which the decolorizing agent should be applied to the partially decolorized sample to substantially decolorize the superficially stained entities without substantially decolorizing the stained entities. As described herein, in some such system embodiments, the flow chamber may be further configured for applying the decolorizing agent to the partially decolorized sample for the determined exposure time so as to prepare a substantially decolorized sample wherein the superficially stained entities, if present, are substantially decolorized and wherein the stained entities, if present, are not substantially decolorized.

In some such system embodiments, the imaging system may be further configured for recording a fourth image of the substantially decolorized sample and subsequently generating a third difference image by comparing the fourth image to the second image. The third difference image may depict the location of at least one of the superficially stained entities. The imaging system may also be configured for generating a fourth difference image by comparing the fourth image to the first image, wherein the fourth difference depicts a location of at least one of the stained entities.

Thus the methods and systems for performing staining procedures for biological materials, as described in the embodiments of the present invention, provide many advantages that may include, but are not limited to: providing methods and systems that are capable of monitoring discernible optical changes in a sample during a staining process so as to better control and/or optimize the staining and decolorization of the sample; providing methods and systems that may be especially capable of classifying and locating Gram-stained entities within a sample by monitoring optical changes that may be discernible between staining and/or decolorization steps and highlighting those optical changes that are unique to Gram-positive and/or Gram-negative entities within the sample; providing systems and methods that may be uniquely capable of minimizing "false positives" and/or "false negatives" when analyzing stained samples in search of entities of interest within the sample (such as disease-causing bacteria, for example); and providing an optimized staining method and system that may be monitored and/or controlled in real time by an optical imaging apparatus. Thus, various embodiments of the present invention may also provide an "all-in-one" staining apparatus and sample analysis tool wherein finished (and optimized) stained sample slides may remain on the same imaging apparatus for downstream morphological investigations. This complete integration of the sample preparation (i.e. staining) steps and analysis steps may allow for more efficient laboratory throughput.

BRIEF DESCRIPTION OF THE SEVERAL
VIEWS OF THE DRAWING(S)

Having thus described the invention in general terms, reference will now be made to the accompanying drawings, which are not necessarily drawn to scale, and wherein:

FIGS. 1-10 show a series of "single-line" images recorded of a sample containing both stained (i.e. Gram-positive, for example) and superficially stained (i.e. Gram-negative, for example) entities, according to one embodiment of the present invention;

FIG. 11 shows a non-limiting depiction of a "single line" image of an unstained sample, corresponding to a first image, produced according to one embodiment of the present invention;

FIG. 12 shows a non-limiting schematic of a "single line" of a sample, showing the locations of stained entities (i.e. Gram-positive entities) in the sample, according to one embodiment of the present invention;

FIG. 13 shows a non-limiting schematic of a "single line" of a sample, showing the lack of superficially stained entities (i.e. Gram-negative entities) in the sample, according to one embodiment of the present invention;

FIG. 14 shows a non-limiting depiction of a "single line" image of a stained sample, corresponding to a second image, produced according to one embodiment of the present invention;

FIG. 15 shows a non-limiting depiction of a "single line" image of a sample, corresponding to a first difference image, produced according to one embodiment of the present invention, highlighting the locations of stained entities in the sample;

FIG. 16 shows a non-limiting depiction of a "single line" image of a sample, corresponding to a third image, produced according to one embodiment of the present invention after a 35% decolorization of the sample;

FIG. 17 shows a non-limiting depiction of a "single line" image of a sample, corresponding to a second difference image, produced according to one embodiment of the present invention, further depicting the lack of superficially stained entities in the sample;

FIG. 18 shows a non-limiting depiction of a "single line" image of a sample, corresponding to a third difference image, produced according to one embodiment of the present invention, highlighting the lack of superficially stained (i.e. Gram-negative, for example) entities in the sample;

FIG. 19 shows a non-limiting depiction of a "single line" image of a sample, corresponding to a fourth difference image, produced according to one embodiment of the present invention, highlighting the locations of stained entities (i.e. Gram-positive, for example) in the sample;

FIG. 20 shows a non-limiting depiction of a "single line" image of an unstained sample, corresponding to a first image, produced according to one embodiment of the present invention;

FIG. 21 shows a non-limiting schematic of a "single line" of a sample, showing the lack of stained entities (i.e. Gram-positive entities) in the sample, according to one embodiment of the present invention;

FIG. 22 shows a non-limiting schematic of a "single line" of a sample, showing the locations of superficially stained entities (i.e. Gram-negative entities) in the sample, according to one embodiment of the present invention;

FIG. 23 shows a non-limiting depiction of a "single line" image of a stained sample, corresponding to a second image, produced according to one embodiment of the present invention;

FIG. 24 shows a non-limiting depiction of a "single line" image of a sample, corresponding to a first difference image, produced according to one embodiment of the present invention, highlighting the locations of superficially stained entities in the sample;

FIG. 25 shows a non-limiting depiction of a "single line" image of a sample, corresponding to a third image, produced according to one embodiment of the present invention after a 35% decolorization of the sample;

FIG. 26 shows a non-limiting depiction of a "single line" image of a sample, corresponding to a second difference image, produced according to one embodiment of the present invention, highlighting the effect of the 35% decolorization on superficially stained entities in the sample;

FIG. 27 shows a non-limiting depiction of a "single line" image of a sample, corresponding to a fourth image, produced according to one embodiment of the present invention, after a 100% decolorization of the sample;

FIG. 28 shows a non-limiting depiction of a "single line" image of a sample, corresponding to a third difference image, produced according to one embodiment of the present invention, highlighting the locations of superficially stained (i.e. Gram-negative, for example) entities in the sample;

FIG. 29 shows a non-limiting depiction of a "single line" image of a sample, corresponding to a fourth difference image, produced according to one embodiment of the present invention, highlighting the lack of stained entities (i.e. Gram-positive, for example) in the sample;

DETAILED DESCRIPTION OF THE INVENTION

Figure 1:
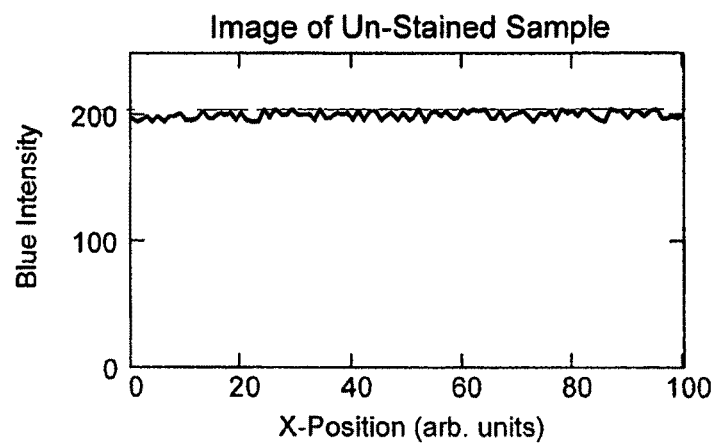
FIG. 1 shows a non-limiting depiction of a "single line" image of an unstained sample, corresponding to a first image, produced according to one embodiment of the present invention.

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

While the various method and system embodiments disclosed herein are described in the context of a Gram staining procedure, it should be understood that the various method and system embodiments described herein may also be applied to many other staining procedures that may cause optical and/or colorimetric changes in a sample. Furthermore, it should be emphasized that the exemplary images shown in FIGS. 1-29 represent only one line of a two-dimensional image. In reducing the various method and system embodiments of the present invention to practice one may deal with many such lines, combined into two-dimensional images of a sample operably engaged with a slide, for example. Also, as described further herein, in some embodiments, a user may utilize the imaging system (and/or a camera device 8 included therein) to record images in more than one field on the sample slide to locate and classify multiple bacteria or other stained and superficially stained entities in the sample.

It should also be understood that the terms "recording images" as used herein are not limited to analog imagery captured by a camera, for example. More particularly, in some embodiments, "recording images" may refer to the capture of data that is indicative of an image and/or corresponds to an image. For example, "recording images" may comprise, in some embodiments, collecting digital data corresponding to color and/or light intensity at one or more points on a surface.

It should be understood that various method and system embodiments of the present invention take advantage of the fact that staining processes (such as Gram staining, for example) may produce discernible and/or detectable optical changes in a sample. By monitoring such changes during the staining process directly on a surface (such as a microscopic slide) with which the sample is operably engaged, the steps of staining and subsequent decolorization can be controlled and optimized. This aspect of the present invention may apply, in particular, to decolorization steps. For example, it is known that in Gram staining processes, too little decolorization may yield false Gram-positives, and that too much decolorization may yield false Gram-negatives. As described herein, various embodiments of the present invention may aid in improving the degree of decolorization in a variety of staining processes (including, for example, Gram staining processes).

It should be further understood that various embodiments of the present invention may also utilize difference images (see, for example, FIGS. 5, 7, 9, 10) to highlight discernible and/or detectable optical changes that may occur differently for Gram-positive entities and Gram-negative entities in the sample, allowing for classification of these entities (which may include, but are not limited to, Gram-stained bacterial entities). As described further herein, various system and method embodiments of the present invention may allow for the accurate determination of specific locations for Gram-positive bacteria, if present, and/or Gram-negative bacteria on the surface with which a sample is operably engaged (such as a typical microscope slide) by analyzing, for example, various difference images generated by comparing images of the slide taken before and after a partial decolorization step (see step 107, FIG. 30, for example) and/or before and after a complete decolorization step (see step 112, FIG. 30, for example).

Figure 30:
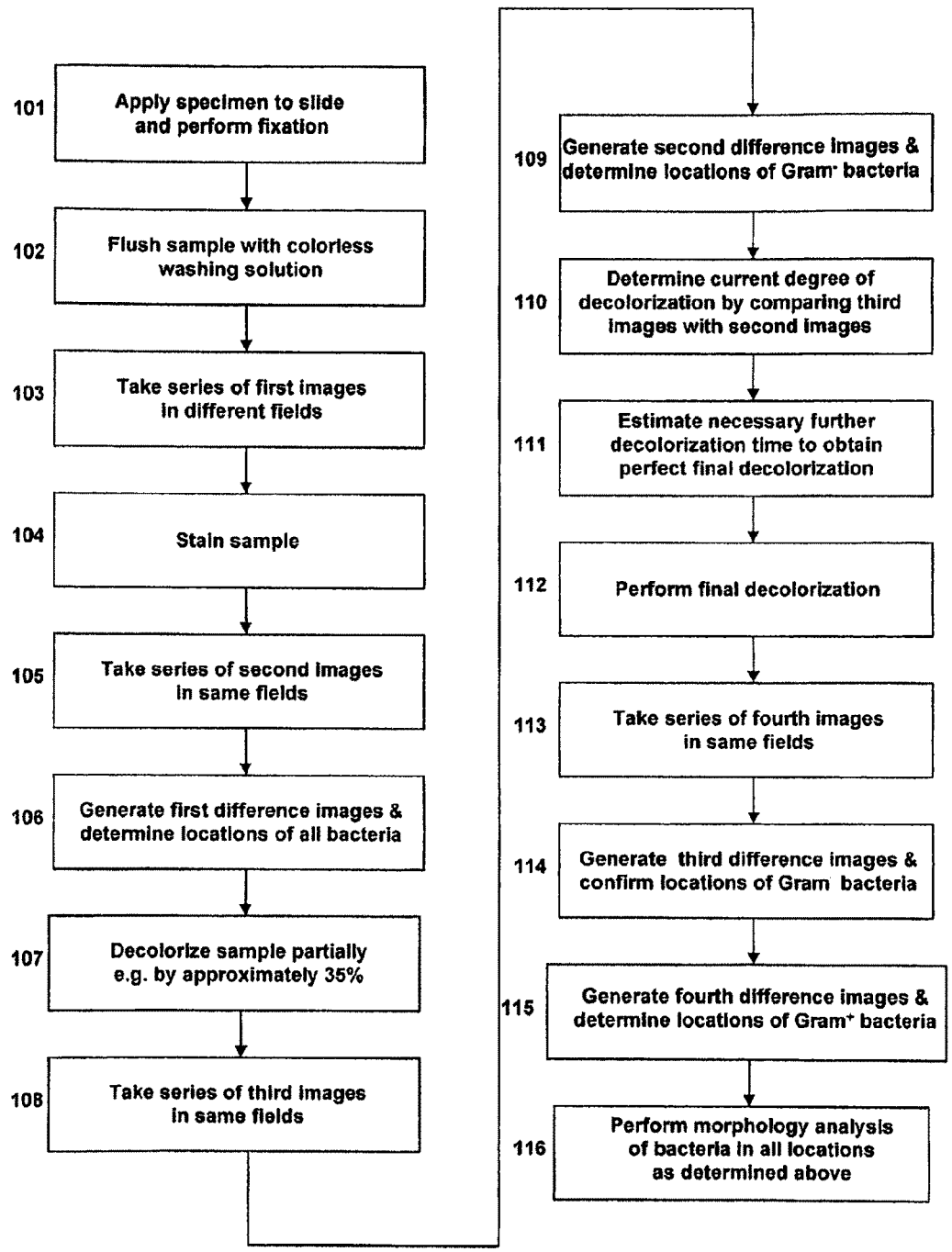
FIG. 30 shows a non-limiting flow chart summarizing method steps for performing a staining procedure for a sample, according to one embodiment of the present invention.
Figure 34:
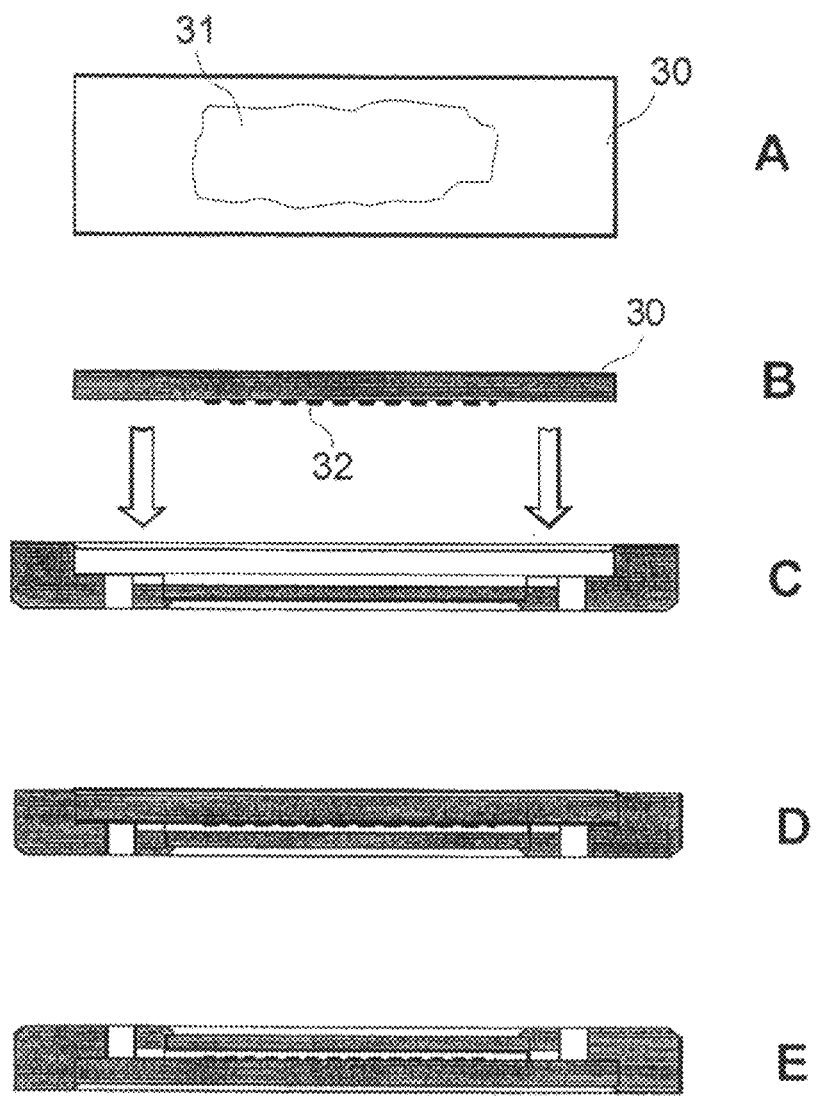
FIG. 34 shows several non-limiting views of a flow chamber, according to one embodiment of the present invention, showing steps for operably engaging a slide with a flow channel housing of the flow chamber.
Figure 35:
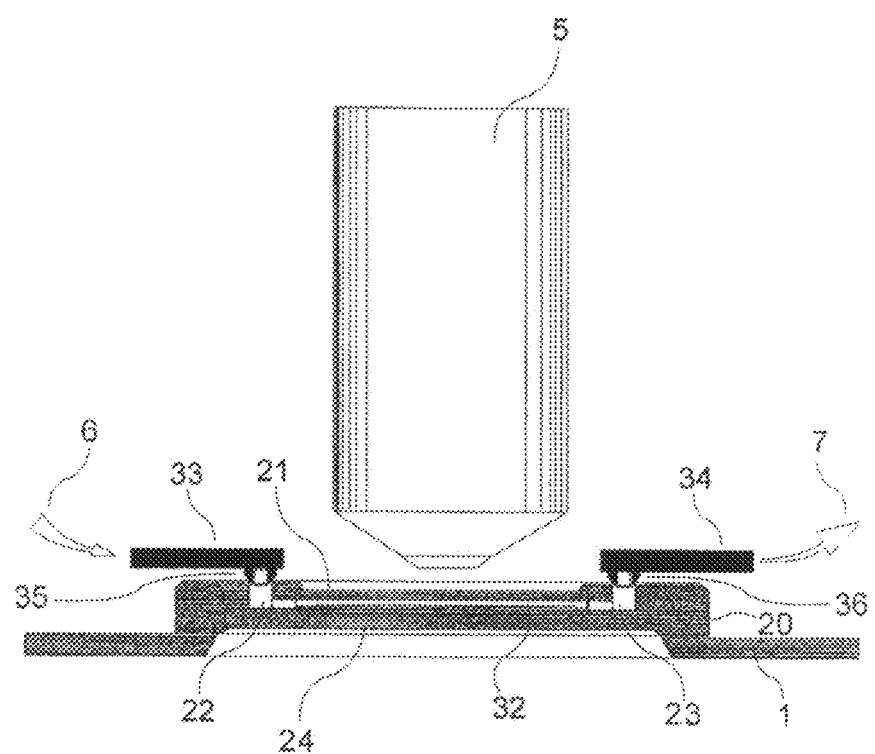
FIG. 35 shows a non-limiting schematic of a flow chamber and an imaging system disposed adjacent to the flow chamber, according to one embodiment of the present invention.

As shown generally in FIG. 30, various embodiments of the present invention may provide methods for performing a staining procedure (such as a Gram staining procedure, for example) for a sample (see, element 32, FIGS. 34 and 35, for example). In one embodiment, the method comprises step 103 for recording a first image of the sample 32. FIG. 1 shows an exemplary first image of the sample 32 generated in a method embodiment used to optimize a Gram staining process where Gram-positive bacteria as well as Gram-negative bacteria are present in an unstained sample 32 that is fixed onto a surface 30 (defined by a microscope slide, as shown in FIG. 34, for example). According to various embodiments of the present invention, step 103 may comprise recording a series of first images in different fields on the unstained sample 32. It should be understood that FIG. 1 shows an exemplary one line across a first image. Because other method steps for applying a staining reagent (see step 104, FIG. 30, for example) may comprise colorizing the entities in the sample with a generally blue color, the first image shown generally in FIG. 1 may be recorded in step 103 using a blue color filter disposed between the sample 32 and a camera device (such as a CCD camera (see elements 5 and 8 of FIG. 32, for example).

Figure 2:
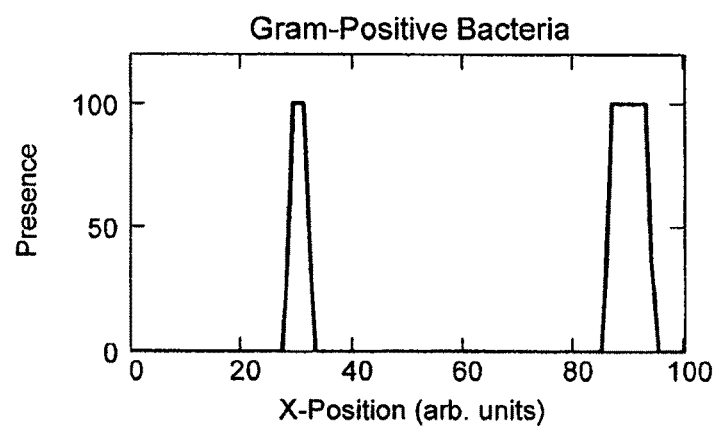
FIG. 2 shows a non-limiting schematic of a "single line" of a sample, showing the locations of stained entities (i.e. Gram-positive entities) in the sample, according to one embodiment of the present invention.
Figure 3:
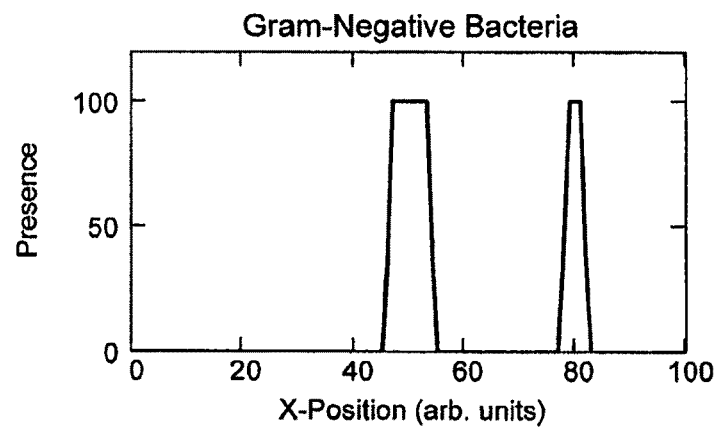
FIG. 3 shows a non-limiting schematic of a "single line" of a sample, showing the locations of superficially stained entities (i.e. Gram-negative entities) in the sample, according to one embodiment of the present invention.

The first image of FIG. 1 may serve as a "baseline" image from which a first difference image (see FIG. 5, for example) may be produced (by comparing a second image of the stained sample (FIG. 4) to the first image (FIG. 1). It should be understood for the purposes of this example that FIGS. 2 and 3 show the positions of stained and superficially stained entities within the sample (corresponding, for example, to Gram-positive and Gram-negative bacteria, respectively, present in the sample). For example, FIG. 2 is a symbolic illustration indicating the locations of Gram-positive bacteria present in the sample along the same one line image field described above with respect to FIG. 1. The word "Presence" on the Y-axis means in the context of FIG. 2 that a functioning detector (such as an imaging system and/or camera device 8, for example) for detecting Gram-positive bacteria with spatial resolution would produce a signal at the X-positions indicated on the X-axis of FIG. 2. Furthermore, FIG. 3 is a symbolic illustration indicating the locations of Gram-negative bacteria present in the sample along the one line image field described above with respect to FIG. 1. The word "Presence" on the Y-axis means in the context of FIG. 3 that a functioning detector (such as an imaging system, for example) for detecting Gram-negative bacteria with spatial resolution would produce a signal at the X-positions indicated on the X-axis of FIG. 3.

As shown generally in FIG. 30 various sample preparation steps may be performed prior to step 103 for recording one or more first images as shown in FIG. 1. For example, some method embodiments may comprise step 101 for applying the sample or specimen to a surface (such as a microscopic slide) and fixing the sample thereto. For example, in some embodiments, the sample 32 (see FIG. 34, for example) may be disposed and thermo-fixed (via the application of subtle heat, for example) onto microscope slide 30 defining a surface within a typical sample attachment area 31. FIG. 34B is an exemplary side view of slide 30 with a sample 32 attached.

As described herein with respect to various system embodiments of the present invention, the prepared slide 30 may then be "snapped" into a flow channel housing (see generally FIGS. 34B and 34C) defining a slide aperture configured for receiving the slide 30 such that the sample 32 is disposed substantially between the slide 30 and the flow channel housing when the slide is disposed in the slide aperture. As described further herein, the flow channel housing may comprise a substantially translucent material such that an imaging system 5 (see FIG. 35, for example) may be capable of recording images of the sample while the sample is disposed between the slide 30 and the flow channel housing. The flow channel housing may comprise a disposable body structured so that the snapped-in microscope slide 30 and a cover glass, which may be integrated into the body, may form a flow-through cell for the application of washing solutions (see step 102, for example), decolorizing reagents (see steps 107 and 112, for example) and/or the application of staining reagents (see step 104, for example). The resulting flow-through cell (or flow channel, as described further herein) may comprise an inlet port and an outlet port for the washing, decolorizing, and staining reagents. One example of a completed disposable flow channel is shown generally in FIG. 34D, and is shown oriented for positioning on an imaging system stage (such as a microscope stage, for example) in FIG. 34E.

It should be understood that the various method steps for washing (step 102), applying a staining agent (step 104), and applying a decolorizing agent (steps 107 and 112, for example) may be accomplished by a variety of washing and/or fluid application techniques other than those described herein with respect to the flow chamber system embodiments depicted, for example in FIGS. 34D and 34E. For example, application of washing solutions, staining agents, and/or decolorizing agents may be accomplished by a variety of known laboratory procedures including, but not limited to: pipetting; aspiration; mixing; centrifuging; and combinations of such processes.

Furthermore, as shown generally in FIG. 30, some method embodiments may further comprise step 102 for washing the sample with a washing solution prior to recording the first image of the sample. For example, step 102 may comprise introducing a substantially colorless washing solution into a flow channel or other space defined between the surface on which the sample 32 is operably engaged and a cover slip (and/or a flow channel housing configured for receiving a microscope slide defining the surface). The washing solution may be flushed through the flow channel in order to "condition" or "prime" the sample, by bringing it (and the biological entities making up the sample) into contact with a liquid. The washing step 102 may be important for the later steps of comparing the various images with each other (i.e. when generating difference images) because step 102 may ensure that the various entities within the sample properly and characteristically absorb and/or superficially absorb the staining agent that may be applied, for example, in step 104 (as described further herein). Furthermore, the washing step 102 may also advantageously fill the space between the sample and a cover slip (or flow channel housing) with the substantially colorless washing fluid which may, in turn, provide also for improved imaging conditions when recording images (see step 103, for example) of the sample.

As is known to persons skilled in the art of Gram staining, each staining step and each decolorizing step comprises a partial step of washing the sample with a washing solution such as water to remove any excess of staining dye or decolorizing reagent. For simplicity, we do not mention these partial steps and consider them as being an integral part of a staining step and/or a decolorization step. Washing step 102, which is applied prior to any staining or decolorizing step, is the only exemption, and is mentioned therefore.

Referring again to FIG. 30, after a baseline first image (see FIG. 1, for example) of an unstained sample is recorded (in step 103, for example) various method embodiments of the present invention may further comprise step 104 for applying a staining agent to the sample so as to prepare a stained sample comprising a plurality of stained entities. The plurality of stained entities may include at least one of a plurality of stained entities (wherein the staining agent is absorbed by the entity (i.e. Gram-positive bacteria, for example) and a plurality of superficially stained entities (wherein the staining agent is merely present on an exterior surface of the entity (i.e. Gram-negative bacteria, for example)). As described herein with respect to various system embodiments of the present invention, step 104 for applying the staining agent may be accomplished by flushing the staining agent through a flow channel (defined in part by a surface with which the sample may be operably engaged) in order to stain the sample. Furthermore, as described herein, the staining agent applied in step 104 may comprise a Gram stain. According to such embodiments, the superficially stained entities may comprise a plurality of Gram-negative entities, and the stained entities may comprise a plurality of Gram-positive entities. In addition, it should be understood that the staining agent applied in step 104 may comprise a variety of staining agents that may be appropriate for preparing a sample for downstream imaging and morphological examination. For example, the staining agent may include, but is not limited to, a reagent comprising crystal violet and Gram's iodine.

Figure 4:
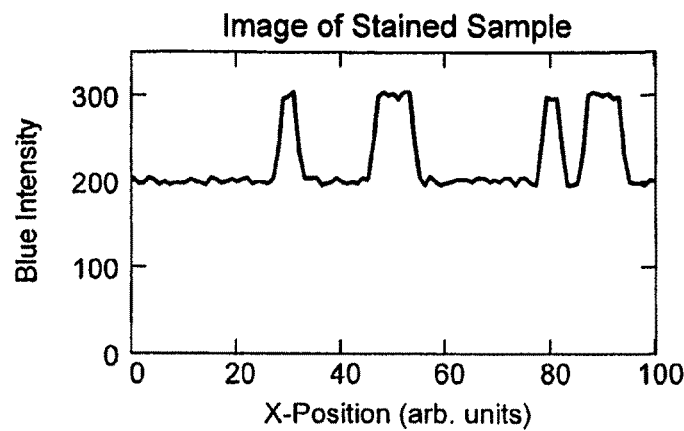
FIG. 4 shows a non-limiting depiction of a "single line" image of a stained sample, corresponding to a second image, produced according to one embodiment of the present invention.

After a staining agent is applied to the sample (in step 104, for example), some method embodiments may further comprise step 105 for recording a second image of the stained sample. An exemplary second image along the same one line image field described above with respect to FIG. 1 is shown, for example, in FIG. 4. FIG. 4 shows the locations of all bacterial entities (Gram-positives as well as Gram-negatives, for example) that are present along the one line. Depending on the detailed features of the first image shown in FIG. 1, the "visibility" of the entities in FIG. 4 may be more or less optimal depending on the structured background signal that may be present.

Figure 5:
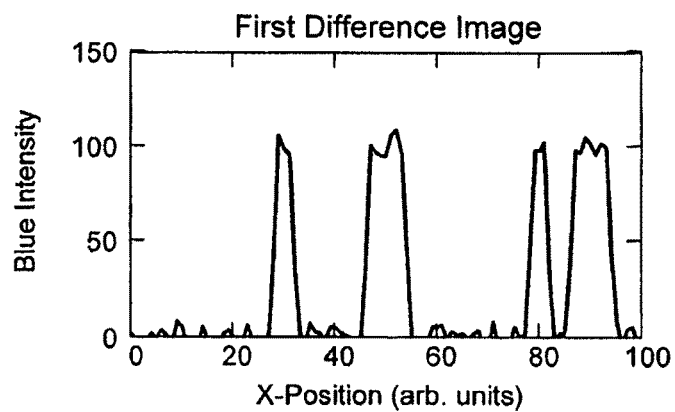
FIG. 5 shows a non-limiting depiction of a "single line" image of a sample, corresponding to a first difference image, produced according to one embodiment of the present invention, highlighting the locations of stained and superficially stained entities in the sample.

Referring again to FIG. 30, the method may further comprise step 106 for generating a first difference image (see FIG. 5) by comparing the second image (see FIG. 4, for example) to the first image (see FIG. 1, for example) so as to determine a location of at least one of the stained entities (if present) on the surface of the slide. The first difference image generated in step 106 (and shown, for example, in FIG. 5), shows that the visibility of the bacteria or other entities present in the sample can be significantly enhanced according to various embodiments of the present invention by generating a first difference image. The first difference image may be produced in step 106 by an image processing computer 18 in communication with an imaging system comprising a camera 8 (see FIG. 32, for example). For example, step 106 may be performed by the image processing computer 18 performing an image processing step (such as image subtraction for example) between the second image (see FIG. 4, for example) and the first image in (see FIG. 1, for example). By performing such an image processing step (such as image subtraction), many of the image features that are not influenced by a Gram staining step may be removed from the first difference image (as shown in FIG. 5, for example). As described herein with respect to the various system embodiments of the present invention, a difference image signal (S) may be generated using an image processing algorithm in the form: $S=(J1-J2)/(J1+J2)$; wherein J1 and J2 refer to signal intensities in primary and secondary images, respectively.

Therefore, only features related to the present entities (such as bacteria), and that are responsive to the staining procedure, are shown in the first difference image of FIG. 5, whereas the structured background signal (generally visible in the first image of FIG. 1) is removed. The first difference image (FIG. 5, for example) illustrates a technical effect of one embodiment of the method of the present invention as it highlights and enhances visualization of the locations of stained and/or superficially stained entities (such as Gram-positive and Gram-negative bacteria, for example) on a slide. This enhancement effect is particularly valuable for possible later visual inspection of the images (such as a morphology analysis (see step 116, for example)).

Figure 6:
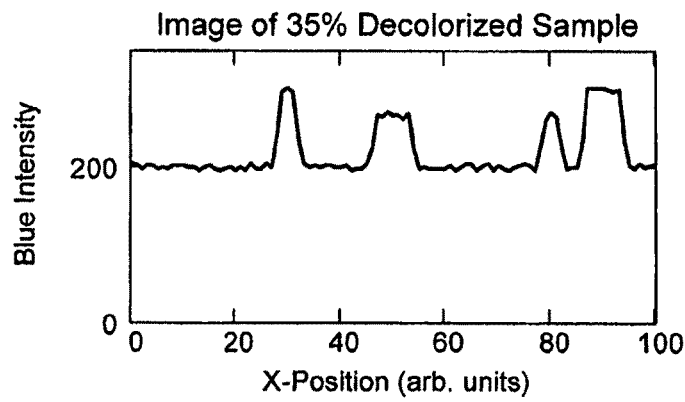
FIG. 6 shows a non-limiting depiction of a "single line" image of a sample, corresponding to a third image, produced according to one embodiment of the present invention after a 35% decolorization of the sample.

Various method embodiments may also comprise step 107 for applying a decolorizing agent to the stained sample so as to prepare a partially decolorized sample wherein at least a portion of the staining reagent is removed from the superficially stained entities. According to one exemplary embodiment, FIG. 6 shows a third image that has been recorded after performing a partial decolorization (see step 107, for example) of the sample, in this case a decolorization by approximately 35% of total decolorization. According to various embodiments, step 107 may also comprise controlling the degree of decolorization that may be performed, e.g., by timing the duration of flushing the space in between the slide 2 and the cover slip 3 (see FIG. 31, for example) with a decolorizing agent such as acid alcohol. As can be seen from the plot in FIG. 6, the signals corresponding to superficially stained entities (comprising Gram-negative bacteria, for example) at X-positions 50 and 80 may be decreased somewhat by the addition of the decolorizing agent in step 107. A certain percentage of decolorization may also be apparent for the stained entities (corresponding to Gram-positive bacteria, for example) that may also be present in the sample, but the decolorization of stained entities is generally much less pronounced, compared to the decolorization of superficially stained entities (corresponding to Gram-negative bacteria, for example). FIG. 30 also shows step 108 for recording a third image of the partially decolorized sample. Step 108 generally results in a third image shown, for example, in FIG. 6.

Figure 7:
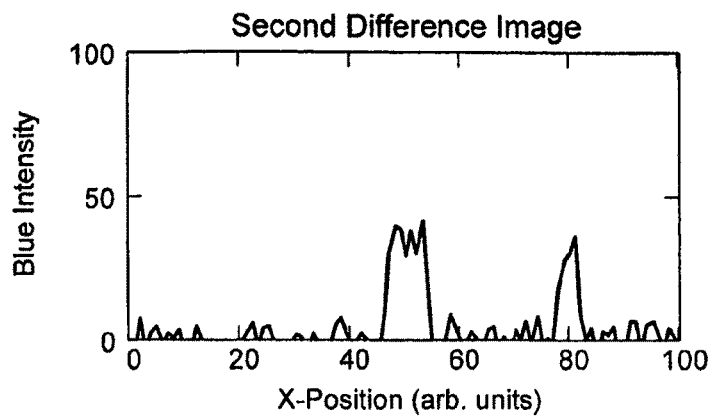
FIG. 7 shows a non-limiting depiction of a "single line" image of a sample, corresponding to a second difference image, produced according to one embodiment of the present invention, highlighting the effect of the 35% decolorization on superficially stained entities in the sample.
Figure 31:
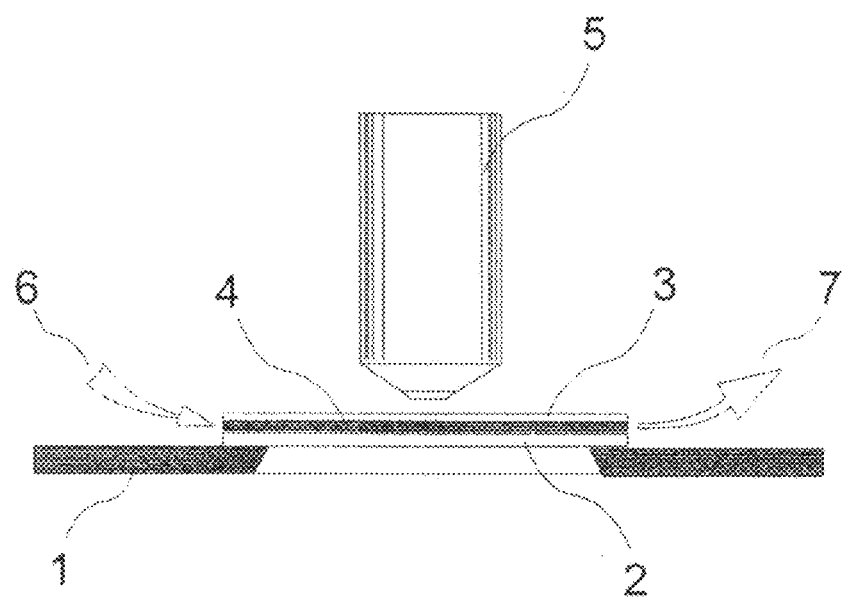
FIG. 31 is a non-limiting schematic depiction of a system according to one embodiment of the present invention, showing an imaging system disposed adjacent to a flow chamber configured for applying a staining agent and/or a decolorizing agent to a sample.

Some method embodiments, as shown generally in FIG. 30, may further comprise step 109 for generating a second difference image (see FIG. 7, for example) by comparing the third image (see FIG. 6, for example) to the second image (see FIG. 4, for example) so as to determine a location of at least one of the superficially stained entities on the surface of the slide 2 (see FIG. 31, for example). FIG. 7 depicts such an exemplary second difference image showing only signals related to superficially stained entities (corresponding to Gram-negative bacteria, for example). As described further herein with respect to various system embodiments of the present invention, the second difference image shown in FIG. 7 may be generated by an image processing computer 18 (in communication with a CCD camera 8, for example). For example, the image processing computer 18 may be configured for generating the second difference image (FIG. 7, for example) by performing an image subtraction step (subtracting the third image (FIG. 6) from the second image (FIG. 4, for example) to highlight those entities within the sample that have been most affected (i.e. decolorized) by the addition of the decolorizing agent in step 107). In Gram-staining embodiments, step 109 may reveal and/or highlight the positions of Gram-negative bacteria, which respond most to the decolorization procedure. Step 109 for generating the second difference image also provides the technical effect of allowing a user (and/or the image processing computer 18) to quantitatively and/or qualitatively compare the signals for superficially stained entities (i.e. Gram-negative bacteria) in the plots of FIG. 4 and FIG. 6 and to perform step 110 for determining the current degree of decolorization achieved during the partial decolorization step (step 107, for example).

Thus, as shown in FIG. 30, step 109 for generating the second difference image also provides a basis for comparison to allow for the performance of step 111 for estimating the necessary further decolorization time to obtain an optimized decolorization of the sample. More particularly, in some method embodiments, step 111 may comprise analyzing the second difference image (see FIG. 7, for example) to determine an exposure time during which the decolorizing agent should be applied to the partially decolorized sample to substantially decolorize the superficially stained entities (i.e. Gram-negative bacteria, for example) without substantially decolorizing the stained entities (i.e. Gram-positive bacteria, for example). Step 111 may comprise quantitatively estimating an exposure time for subsequent step 112 to substantially decolorize the superficially stained entities by performing a ratio calculation based at least in part on the exposure time that resulted in the level of decolorization in the superficially stained entities that is apparent from viewing the "blue intensity" of the second difference image shown, for example, in FIG. 7.

Figure 8:
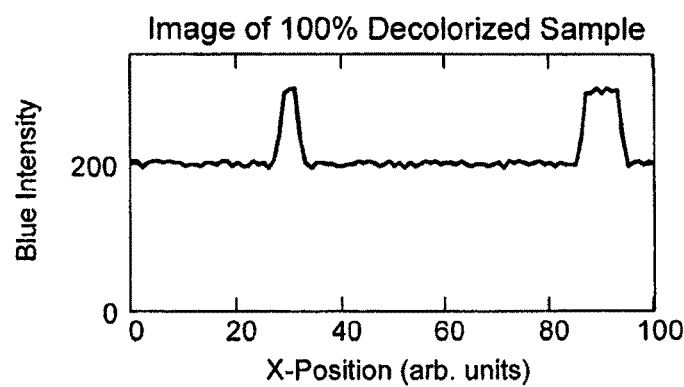
FIG. 8 shows a non-limiting depiction of a "single line" image of a sample, corresponding to a fourth image, produced according to one embodiment of the present invention, after a 100% decolorization of the sample.

Some method embodiments may further comprise step 112 for applying the decolorizing agent (such as acid alcohol, for example) to the partially decolorized sample (for the exposure time determined in step 111) so as to prepare a substantially decolorized sample wherein the superficially stained entities (i.e. Gram-negative bacteria, for example) are substantially decolorized and wherein the stained entities (Gram-positive bacteria, for example) are not substantially decolorized. As shown in FIG. 30, the method may also comprise step 113 for recording a fourth image (see FIG. 8, for example) of the substantially decolorized sample. FIG. 8 shows a fourth image obtained, for example, after applying the final decolorization step (step 112). As shown in FIG. 8, only signals corresponding to stained entities (i.e. Gram-positive bacteria) remain detectable at X-positions 30 and 90 on the slide surface.

Figure 9:
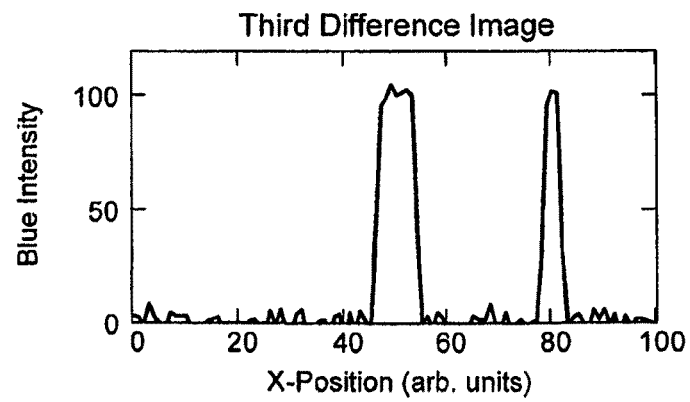
FIG. 9 shows a non-limiting depiction of a "single line" image of a sample, corresponding to a third difference image, produced according to one embodiment of the present invention, highlighting the locations of superficially stained (i.e. Gram-negative, for example) entities in the sample.

Referring again to FIG. 30, various method embodiments may also comprise step 114 for generating a third difference image (see FIG. 9, for example, showing an exemplary third difference image produced by an image processing computer 18 (see FIG. 32)). The third difference image may be produced by comparing the fourth image (see FIG. 8) with the second image (see FIG. 4, for example). In some embodiments, the third difference image of FIG. 9 may be produced by performing an image subtraction procedure to "subtract" the signals detected in the fourth image (FIG. 8) from those detected in the second image (FIG. 4). As shown in FIG. 9, the third difference image may clearly depict the location of at least one of the superficially stained entities (i.e. Gram-negative bacteria, for example) on the surface. In the exemplary plot of the third difference image shown in FIG. 9, the locations of Gram-negative bacteria are depicted at locations 40 and 80 on the slide surface.

Figure 10:
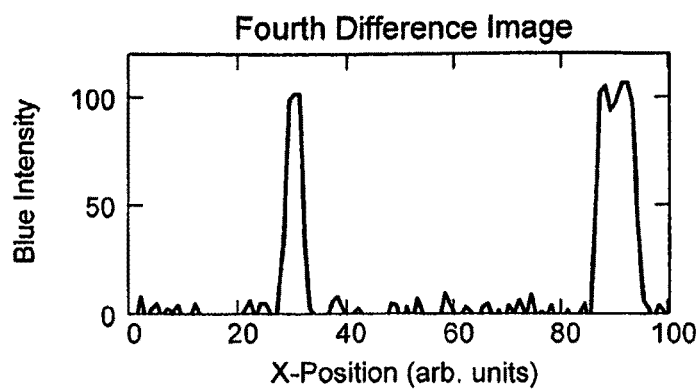
FIG. 10 shows a non-limiting depiction of a "single line" image of a sample, corresponding to a fourth difference image, produced according to one embodiment of the present invention, highlighting the locations of stained entities (i.e. Gram-positive, for example) in the sample.

In order to confirm the locations (i.e. X-positions, for example) of stained entities (i.e. Gram-positive bacteria) on the slide surface, some method embodiments may further comprise step 115 for generating a fourth difference image (see FIG. 10) by comparing the fourth image (FIG. 8) to the first image (FIG. 1). As shown in FIG. 10, the fourth difference may depict a location of at least one of the stained entities on the surface of the slide. In some embodiments, step 115 may be performed by an image processing computer 18 in communication with a CCD camera 8 (or other imaging system component) to subtract the signal plot in FIG. 1 from the signal plot in FIG. 8. The difference image (FIG. 10, for example) shows the signals (and corresponding locations) of Gram-positive bacteria.

In some method embodiments, the third and fourth difference images (in FIGS. 9 and 10, respectively) may be used to perform a more detailed morphology analysis (see step 116) for the purpose of further classification of all entities (i.e. Gram-positive and Gram-negative bacteria, for example) found in the sample 32. Step 116 may be performed, for example, using an image processing computer 18 having an integrated memory device (not shown) configured for storing a library of known entities, in order to aid a user in classifying the various entities (i.e. Gram-negative and Gram-positive bacteria, for example) whose locations have been determined and/or confirmed by the various method steps shown, for example, in steps 101-115 of FIG. 30. For example, step 116 may comprise analyzing a morphology of the superficially stained entities (i.e. Gram-negative bacteria). Furthermore, in some embodiments, step 116 may also comprise analyzing a morphology of the stained entities (i.e. Gram-positive bacteria).

Figure 14:
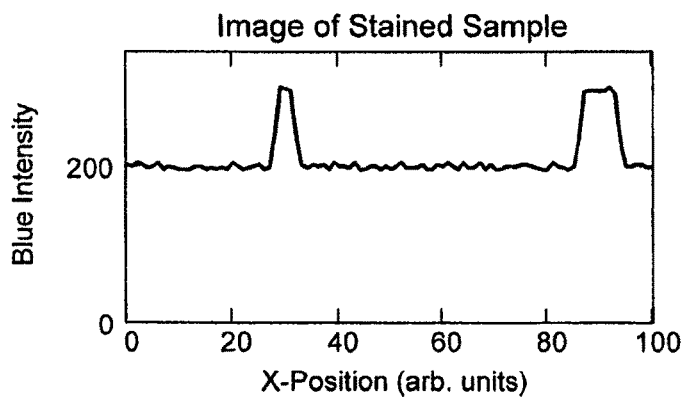

FIGS. 11-19 show various images generated according to the various method steps of the present invention (see FIGS. 30 and 36, generally) in an exemplary case wherein only Gram-positive bacteria are present in the sample 32. Specifically, FIGS. 11-13 correspond fully to FIGS. 1-3, respectively, showing the first image, the locations of Gram-positive bacteria (at X-positions 30 and 90 on the slide surface, for example), and the locations of Gram-negative bacteria (none). Furthermore, FIG. 14 depicts a second image taken after the application of a staining reagent (see step 104, for example), showing only signals corresponding to Gram-positive bacteria.

Figure 11:
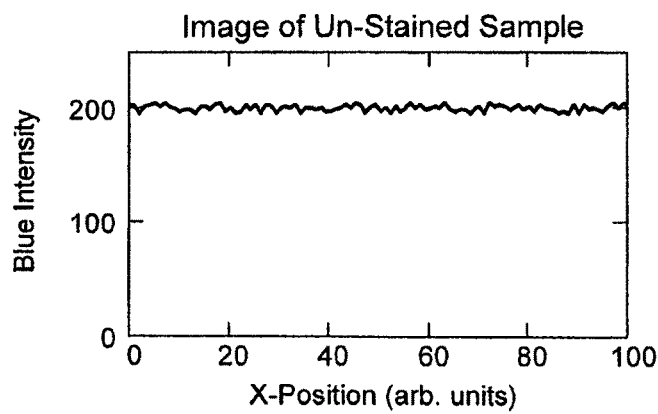
FIGS. 11-19 show a series of "single-line" images recorded of a sample containing only stained (i.e. Gram-positive, for example) entities, according to one embodiment of the present invention.
Figure 12:
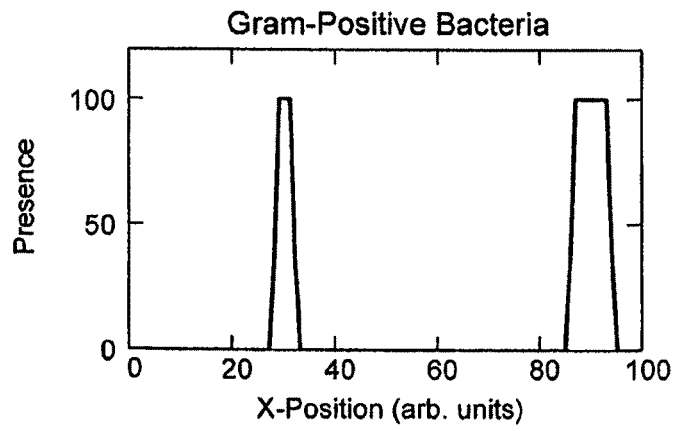
Figure 13:
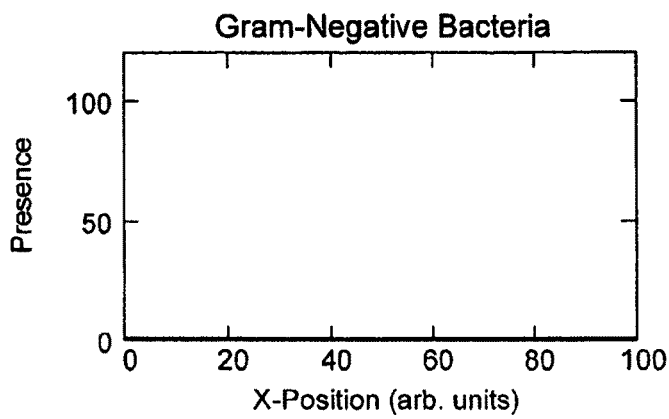
Figure 15:
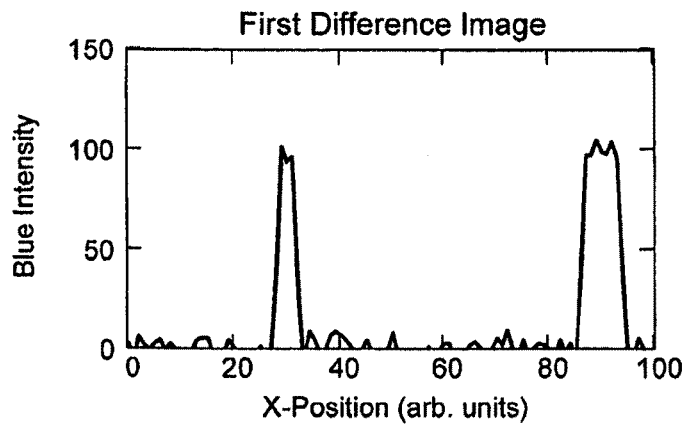
Figure 16:
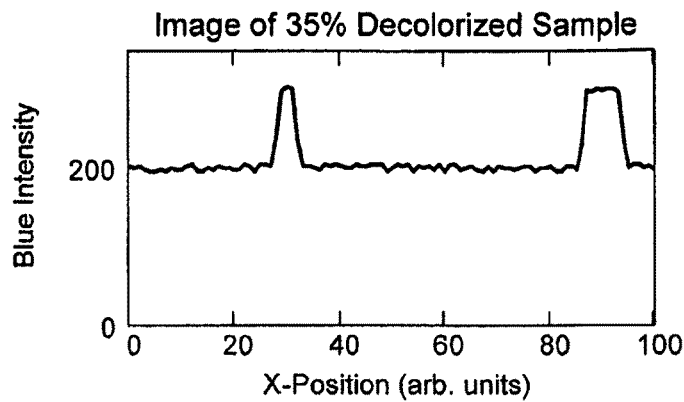
Figure 17:
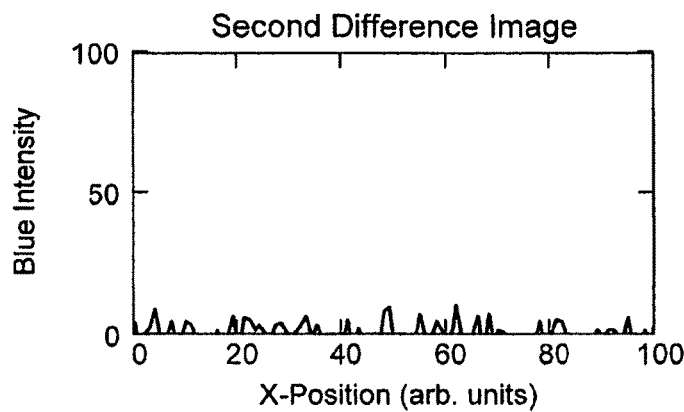
Figure 18:
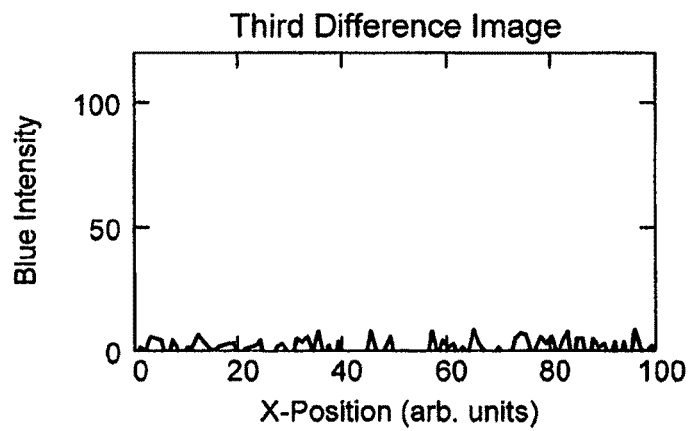
Figure 19:
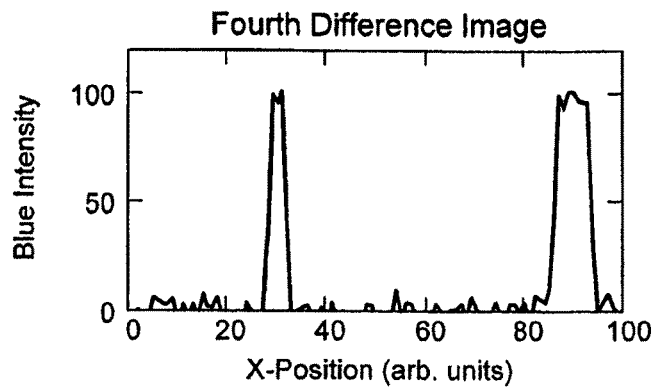
Figure 20:
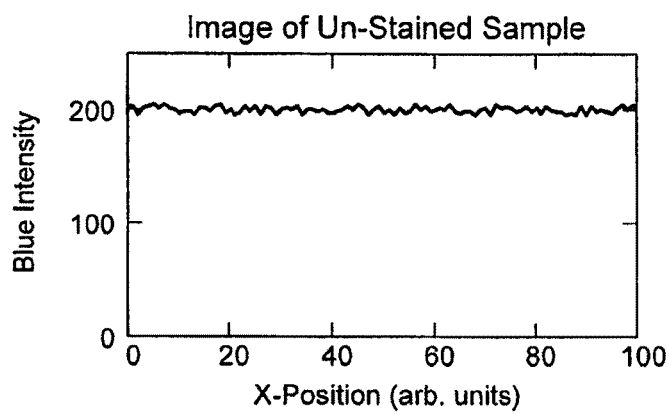
FIGS. 20-29 show a series of "single-line" images recorded of a sample containing only superficially-stained (i.e. Gram-negative, for example) entities, according to one embodiment of the present invention.
Figure 21:
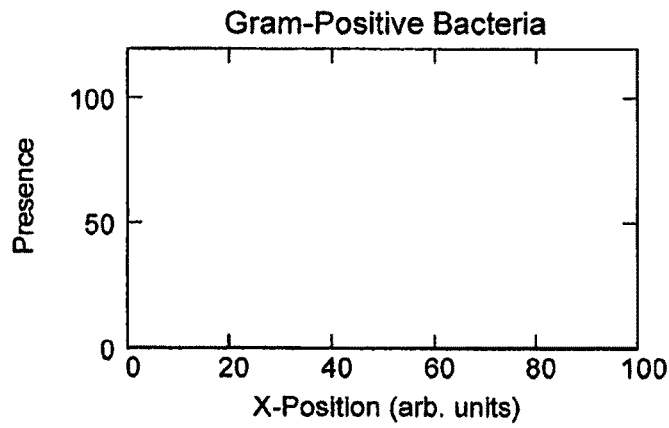
Figure 22:
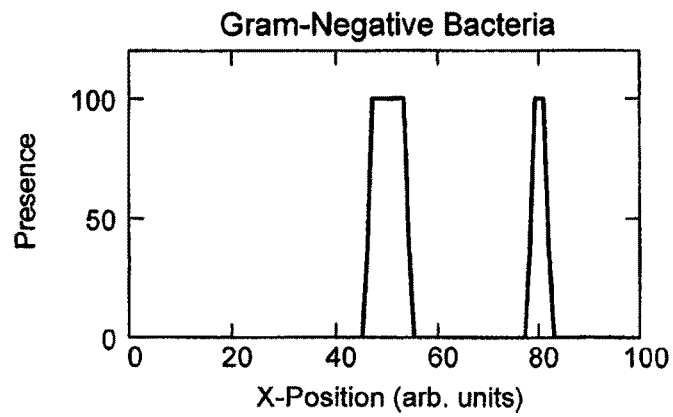

FIG. 15 shows a first difference image with background-free signals (obtained, for example, by subtracting the "background" signal of FIG. 11 from the post-stain image of FIG. 14 in order to highlight the locations of the Gram-positive bacteria. Furthermore, FIG. 16 shows a third image obtained after application of a decolorizing agent to obtain partial decolorization of the sample. FIG. 17 is a second difference image, which would, in some cases, show the signals from Gram-negative bacteria. As expected in this case (from the known data shown in FIG. 13) no signals are present. This result shows that the formal application of the method steps of the present invention (see FIGS. 30 and 36, for example) may provide correct information about the presence or absence of Gram-negative bacteria without significant input from an operator. FIG. 18 is a third difference image, which also would indicate the presence of Gram-negative bacteria, if present. Finally, FIG. 19 shows a fourth difference image showing the signals and locations of Gram-positive bacteria in excellent contrast so as to allow for a more complete morphology analysis of the Gram-positive bacteria (see step 116, FIG. 30, for example).

FIGS. 20-29 show various images generated according to the various method steps of the present invention (see FIGS.

30 and 36, generally) in an exemplary case wherein only superficially-stained entities (i.e. Gram-negative bacteria) are present in the sample 32. Specifically, FIGS. 20-22 correspond fully to FIGS. 1-3, respectively, showing the first image, the locations of Gram-positive bacteria (none), and the locations of Gram-negative bacteria (at X-positions 50 and 80 on the slide surface, for example).

Figure 23:
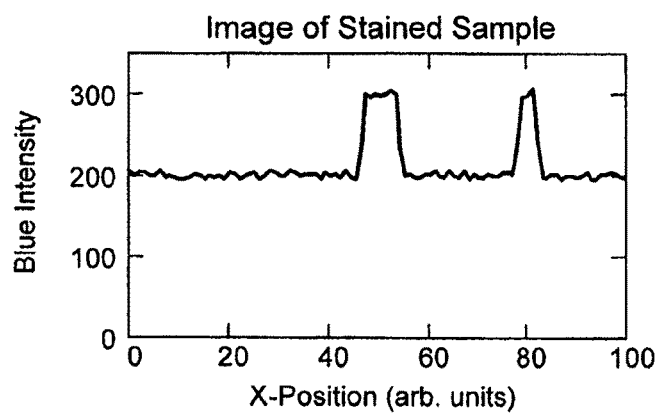
Figure 24:
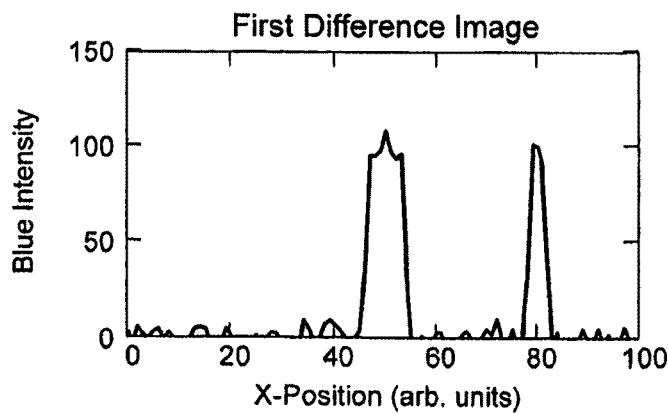
Figure 25:
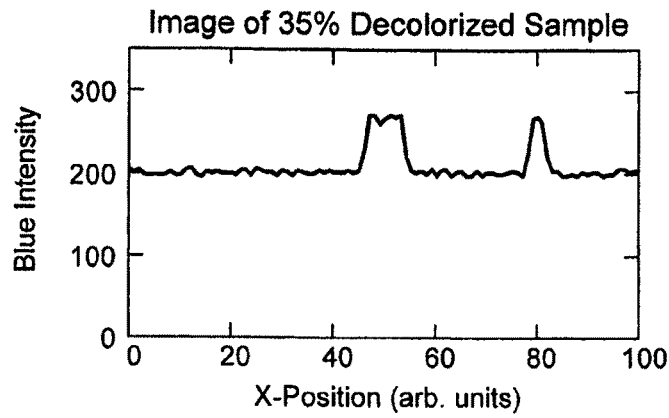

FIG. 23 shows a second image, showing only signals from Gram-negative bacteria after an application of a staining reagent. FIG. 24 shows a first difference image with background-free signals, clearly illustrating the locations of Gram-negative bacteria at X-positions 50 and 80. As described herein with respect to various method and system embodiments, each of the difference images (FIGS. 24, 26, 28 and 29, for example) may be generated by an image processing computer 18 (see FIG. 32) configured for performing an image subtraction procedure using the various images provided by a CCD camera 8 or other imaging system component. FIG. 25 shows a third image obtained after partial decolorization of the sample, which may be achieved via the application of a decolorizing agent (see step 107, FIG. 30, for example).

Figure 26:
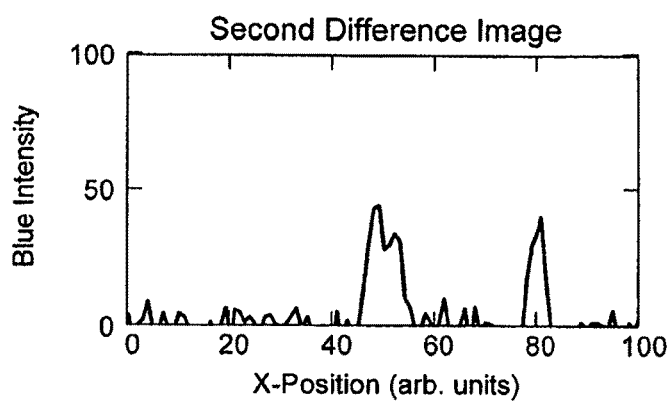
Figure 27:
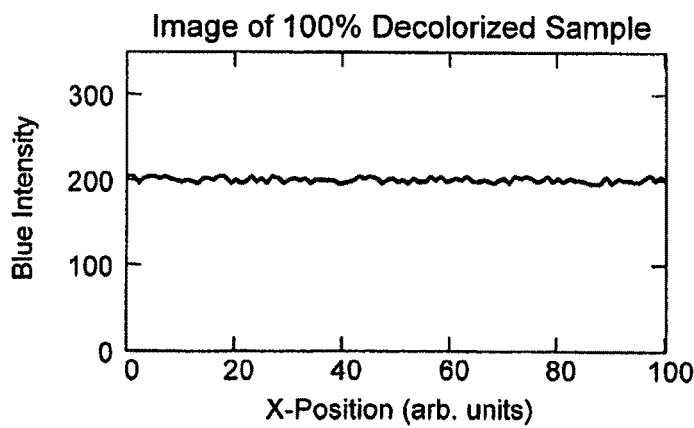
Figure 28:
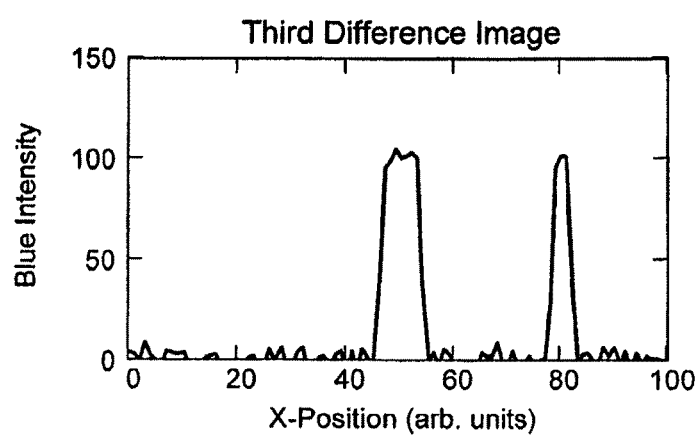
Figure 29:
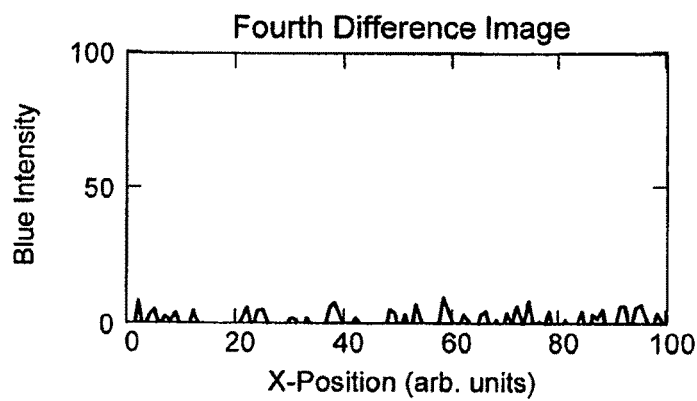

FIG. 26 shows a second difference image, which would show the signals from Gram-negative bacteria. As expected in this case, signals are present. This result shows again that the formal application of the method steps according to various embodiments of the present invention, achieves the technical effect of providing correct information about the presence or absence of Gram-negative bacteria in a sample 32 without the need for substantial input from an operator. FIG. 27 is a fourth image obtained after final decolorization. As expected, no signals from the superficially-stained Gram-negative bacteria are detectable in this image. FIG. 28 is a third difference image, showing the clear presence and location of Gram-negative bacteria on the slide surface. Finally, FIG. 29 is a fourth difference image, which would indicate the presence of Gram-positive bacteria, were such present in the sample. As expected in this case (see FIG. 21), no signals from Gram-positive bacteria are detected.

Figure 36:
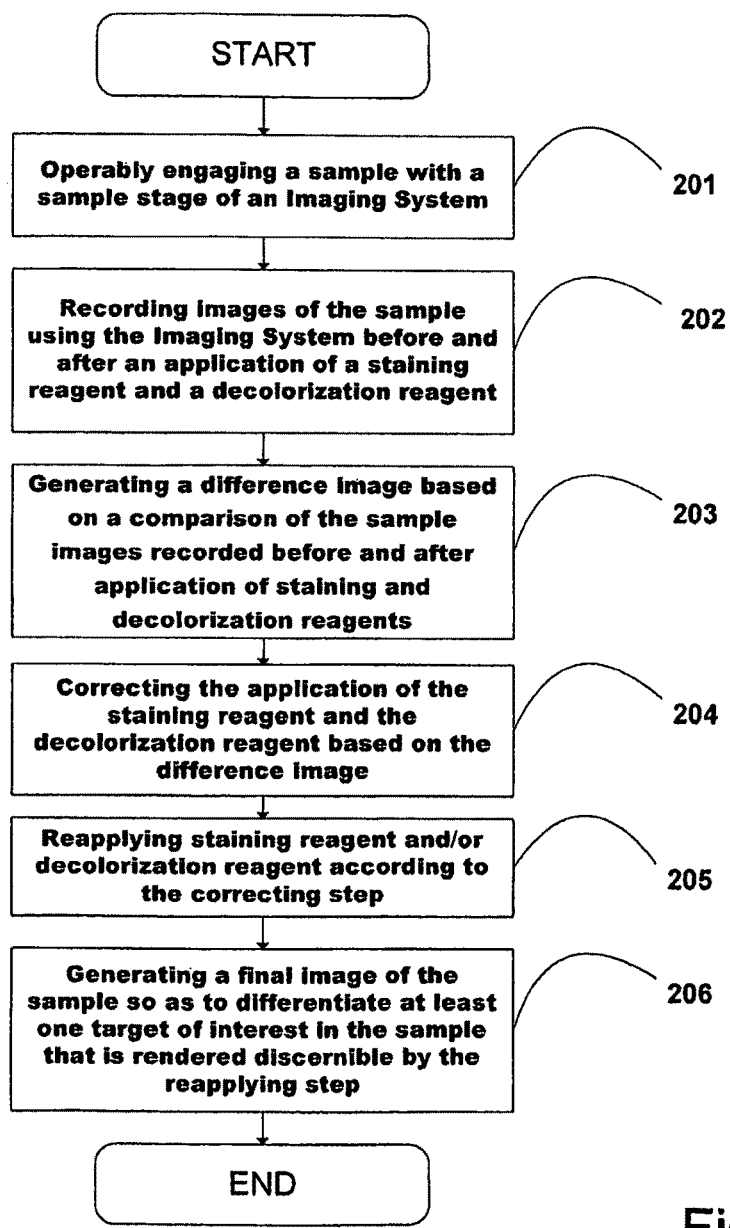
FIG. 36 shows a non-limiting flow chart summarizing method steps for a method for optimally staining a sample, according to one embodiment of the present invention.

FIG. 36 shows a schematic flow chart of a method, according to an alternate embodiment of the present invention for staining a sample. The method first comprises step 201 for operably engaging a sample with a sample stage 1 of an imaging system (see generally, FIG. 35). Step 201 may be accomplished, in some embodiments, as shown generally in FIG. 34. For example, FIG. 34 is an illustration of the sample installation procedure that may be used in one embodiment of the present invention. In FIG. 34A, the sample 32 is disposed and thermo-fixed onto an ordinary microscope slide 30 within a typical sample attachment area 31. FIG. 34B is a side view of slide 30 with a sample 32 attached. The prepared slide 30 is then "snapped" into a disposable body with the one surface having the sample 32 operably engaged therewith (see generally, FIG. 34C). The disposable body is structured so that the snapped-in microscope slide and a cover glass, which is integrated into the body, form a flow chamber 20 for applying at least one of the staining and decolorizing reagents to the sample 32. As shown in FIG. 35, the flow chamber 20 may define a reagent inlet 22, and a reagent outlet 23 for "washing" the decolorizing and staining reagents through the flow chamber 20 and past the sample 32. One embodiment of a completed disposable flow chamber is shown in FIG. 34D. The flow chamber 20 may be inverted for positioning on a microscope stage 1 (see FIGS. 34E and 35).

As shown in FIG. 36, the various method embodiments may also comprise step 202 for recording images of the sample using the imaging system before and after an application of a staining reagent and a decolorization reagent to the sample. For example, step 202 may comprise recording images of the sample at various stages of the staining and/or decolorization processes described herein. The images recorded in step 202 may include, but are not limited to: an image of the unstained sample (see FIG. 1, for example); an image of the stained sample (see FIG. 4, for example); and an image of a partially decolorized sample (see FIG. 6, for example).

The method may further comprise step 203 for generating a difference image based at least in part on a comparison of the images of the sample recorded before and after the application of the staining reagent and the decolorization reagent to the sample. For example, step 203 may comprise, in some embodiments, generating a second difference image (see FIG. 7, for example) by subtracting the image signals of the image of the partially decolorized sample (see FIG. 6, for example) from the image signals present in the image of the stained sample (see FIG. 4, for example).

Referring again to FIG. 36, various method embodiments of the present invention may also comprise step 204 for correcting the application of the staining reagent and/or the decolorization reagent based at least in part on the difference image generated in step 203. For example, step 204 may comprise determining quantitatively the degree of decolorization apparent in the sample (and/or in the superficially-stained entities included therein) by analyzing the difference image of step 203. For example, the measurable "blue intensity" of FIG. 7 generally indicates the quantitative amount of decolorization achieved during the application of a decolorizing agent. Given a known exposure and/or "flushing" time, step 204 may comprise determining a corrected and/or additional exposure time that would be expected to remove the remaining staining reagent from the superficially stained entities present in the sample. The method may further comprise step 205 for reapplying at least one of the staining reagent and the decolorization reagent according to the various parameters (such as exposure and/or flush time) calculated in the correcting step 204. Finally, as shown in FIG. 36, such method embodiments may further comprise generating a final image (see FIG. 8, for example) of the sample so as to differentiate at least one target of interest (i.e. Gram-positive entities) in the sample that may be rendered discernible by the reapplying step 205.

Various embodiments of the present invention may also provide system and/or apparatus embodiments for performing an optimized staining procedure (such as a Gram stain procedure) for a sample 32. For example one system embodiment, shown generally in FIGS. 32 and 35 comprises a flow chamber 20 defining a channel in fluid communication with a supply of a staining agent 11 and a supply of a decolorizing agent 12, wherein the flow chamber comprises a surface 31 configured for operably engaging the sample 32 therewith (see FIGS. 34A-34E, for example). In some system embodiments, the flow chamber may be defined between a slide 2 and cover glass 3 having a spacer 4 operably engaged therebetween to define a flow chamber (as shown generally in FIG. 31 and as described further herein).

As shown generally in FIGS. 34 and 35, the flow chamber 20 may comprise a slide 30 defining the surface 31 for operably engaging the sample 32 therewith. The flow chamber 20 may also comprise a flow channel housing defining a slide aperture adapted for receiving a standard slide (see FIGS. 34B-34C showing the slide being operably engaged with the flow channel housing) such that the sample 32 is disposed substantially between the slide 30 and the flow channel housing when the slide is disposed in the slide aperture. Furthermore, the flow channel housing may comprising a substantially translucent material (such as an integrated glass and/or polycarbonate cover glass 21) such that the imaging system (and/or a lens 5 thereof) may be capable of recording images of the sample 32 while the sample 32 is disposed between the slide 30 and the flow channel housing.

Figure 32:
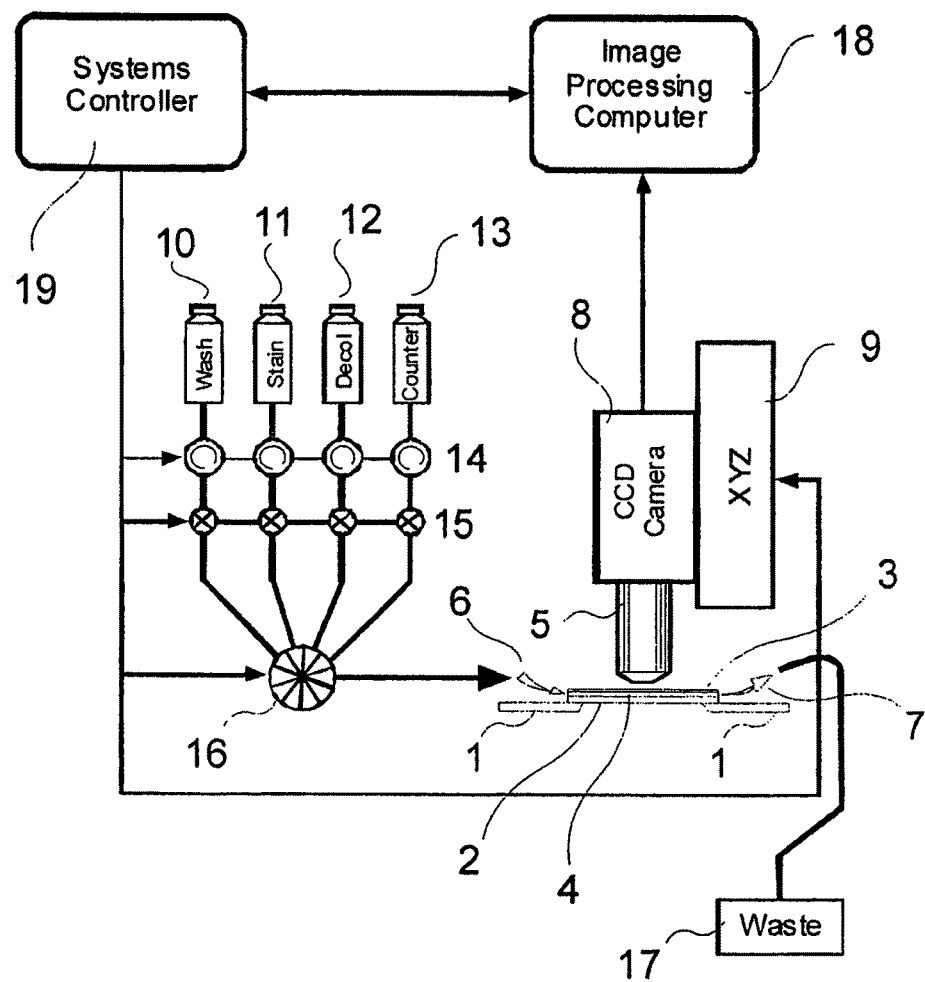
FIG. 32 is a non-limiting schematic depiction of a system according to one embodiment of the present invention, including a flow channel and an imaging system including a camera device, an actuator device, an image processing computer, and a systems controller.

The flow chamber 20 (and/or a systems controller 19 portion of the system in communication therewith) may cooperate with a fluidics system (comprising, for example, various appropriate pumps 14, valves 15, and one/or more combining valves 16, as shown in FIG. 32, for example) that is configured for applying the staining agent to the sample 32 (via a reagent inlet 22, for example) so as to prepare a stained sample comprising a plurality of stained entities. As described herein with respect to various method embodiments, the plurality of stained entities may include at least one of a plurality of stained entities (Gram-positive entities, for example) and a plurality of superficially stained entities (Gram-negative entities, for example). The fluidics system 14, 15, 16 (in cooperation with the flow chamber 20) may be further configured for applying the decolorizing agent to the stained sample (via the reagent inlet 22, for example) so as to prepare a partially decolorized sample wherein at least a portion of the stain is removed from the superficially stained entities. In some system and/or apparatus embodiments, the fluidics system 14, 15, 16 (in cooperation with the flow chamber 20 and/or a systems controller 19) may be further configured for applying the decolorizing agent 12 to the partially decolorized sample for a determined exposure time (calculated, for example, in step 111 of FIG. 30, for example) so as to prepare a substantially decolorized sample wherein the superficially stained entities are substantially decolorized and wherein the stained entities are not substantially decolorized by the application of the decolorizing agent. Furthermore, and as shown generally in FIG. 32, various system embodiments may comprise reservoirs 10, 11, 12, and 13, containing washing, staining, decolorizing, and counter-staining reagents, respectively. The systems controller 19 may be configured for directing these reagents towards reagent inlet 6 of the flow-through disposable (i.e. the flow chamber 20) via appropriate pumps 14, valves 15, and one/or more combining valves 16. Reagents that are flushed through the flow chamber 20 may be collected in a waste reservoir 17 provided in some system embodiments.

System and apparatus embodiments of the present invention may also comprise an imaging system (and/or an objective lens 5 thereof) disposed adjacent to the flow chamber 20 such that the sample 32 is positioned within a field of view of the imaging system. As shown in FIG. 32, the imaging system may comprise: an objective lens 5; an imaging receiver or camera device 8 such as a CCD camera configured to be capable of recording images of the sample while the sample 32 is disposed between the slide 30 and the flow channel housing 20; and an actuator device (such as an XYZ-translation mechanism 9, for example) operably engaged with the camera device 8 and configured for adjusting a position of the camera device 8 relative to the flow chamber 20. It should be understood that, in alternate system embodiments, the system may comprise an actuator mechanism (such as an XYZ-translation mechanism) operably engaged with the stage 1 (see FIG. 32) and configured for adjusting a position of the flow chamber 20 relative to the camera device 8. In some embodiments, the camera device 8 may be in communication with an image processing computer 18 (as described further herein), which may be in communication with a systems controller 19. Furthermore, the systems controller 19 may also be in communication with a control input of the XYZ-translation mechanism 9 to move objective lens 5 to different fields of interest on the sample 32, and to perform auto-focus operations relative to the sample 32.

Because the slide 30 and/or flow chamber 20 are operably engaged with a stage 1 of the imaging system, the components of the imaging system (such as the imaging receiver 8) may be configured for monitoring the sample 32 (in real time), before, after, and/or during an application of at least one of the staining agent and the decolorizing agent. The imaging system (and/or the image processing computer 18 thereof) may be further configured for generating a difference image (see FIG. 7, for example) by comparing at least one image of the sample 32 obtained before a first application of the decolorizing agent (see FIG. 4, for example) and at least one image of the sample obtained after the first application of the decolorizing agent (see FIG. 6, for example).

The imaging system (and/or an image processing computer 18 included therein) may be further configured, in some embodiments, to determine an exposure time (see step 111, FIG. 30, for example) for a second application of the decolorizing agent based at least in part on the difference image (FIG. 7) so as to substantially decolorize the superficially stained entities without substantially decolorizing the stained entities such that the stained entities may be more readily discerned from the superficially stained entities. Various system embodiments may also comprise a controller device (such as the systems controller 19, shown in FIG. 32, for example) in communication with the imaging system 8, 9, 18 and the fluidics system 14, 15, 16. The controller device may be configured for controlling the application of at least one of the staining agent and the decolorizing agent based at least in part on the images generated by the imaging system (comprising, for example, a camera device 8).

In some system embodiments, the imaging system (and/or components thereof (such as the image processing computer 18)) may be configured for performing one or more of the method steps outlined generally in FIGS. 30 and 36. For example, in one embodiment, the imaging system (and/or a camera device 8 thereof) may be configured for performing step 103 for recording a first image (see FIG. 1) of the sample 32. The imaging system may be further configured for recording a second image (see FIG. 4) of the stained sample after applying the staining agent to the sample using the flow chamber 20.

Furthermore, the imaging system (and/or an image processing computer 18 included therein) may be further configured for generating a first difference image (see FIG. 5, for example) by comparing the second image (FIG. 4) to the first image (FIG. 1) so as to determine a location of at least one of the stained entities on the surface 31 of the slide 30. The imaging system (and/or the camera device 8 thereof) may be further configured for recording a third image (FIG. 6, for example) of the partially decolorized sample after applying the decolorizing agent (see step 107, FIG. 30) using the flow chamber 20. The imaging system (and/or the image processing computer 18) may be further configured for generating a second difference image (see FIG. 7) by comparing the third image (FIG. 6) to the second image (FIG. 4) so as to determine a location of at least one of the superficially stained entities. Finally, in some system embodiments, the imaging system (and/or the image processing computer 18 in cooperation with the systems controller 19) may be further configured for performing step 111 for analyzing the second difference image (FIG. 7) to determine an exposure time during which the decolorizing agent is applied to the partially decolorized sample to substantially decolorize the superficially stained entities without substantially decolorizing the stained entities.

According to various system embodiments of the present invention, the imaging system (including various image processing computer 18 and/or camera device 8 components) may be further configured for performing various method steps including, but not limited to: step 113 for recording a fourth image of the substantially decolorized sample (see FIG. 8, for example); step 114 for generating a third difference image (FIG. 9) by comparing the fourth image to the second image; and step 115 for generating a fourth difference image (FIG. 10) by comparing the fourth image to the first image. As described herein with respect to various method embodiments of the present invention, the third difference image (see FIG. 9, for example) may depict the location of at least one of the superficially stained entities (i.e. Gram-negative entities, for example). Furthermore, the fourth difference image (see FIG. 10, for example) may depict a location of at least one of the stained entities (i.e. Gram-positive entities, for example).

As shown in FIG. 32, the imaging system provided in various system embodiments of the present invention may comprise an image processing computer 18 configured for generating difference images that may include, but are not limited to: the first difference image (FIG. 5, for example), the second difference image (FIG. 7, for example), the third difference image (FIG. 9, for example), and the fourth difference image (FIG. 10, for example). In such system embodiments, the image processing computer 18 may be configured for generating one or more of the various difference images using processes that may include, but are not limited to: image subtraction; image addition; image ratio calculation; and combinations of such image processing routines. For example, in some embodiments, the image processing computer 18 (and/or the systems controller 19, in some embodiments) may be configured for generating a difference image signal (S) using an image processing algorithm in the form: $S=(J1-J2)/(J1+J2)$; wherein J1 and J2 refer to signal intensities in primary and secondary images, respectively.

FIG. 31 is a schematic depiction of a system according to one embodiment of the present invention. The biological sample is disposed and fixed onto a microscope slide 2, which may be positioned on the XY-stage 1 of a microscope and is imaged through a microscope objective lens 5 towards an imaging receiver such as a CCD camera (or other camera device 8 (see FIG. 32). A cover glass 3 is held at a selected distance from microscope slide 2 by means of a spacer 4 having an appropriate thickness. The spacer 4 may form a flow channel between slide 2 and cover glass 3 with a reagent inlet 6 on one side and a reagent outlet 7 on another side. The spacer 4 may comprise an elastomeric substance configured to provide substantially fluid-tight engagement between the spacer 4 and the slide 2 as well as between the spacer 4 and the cover glass 3 such that a parallel flow chamber is formed. The effective thickness of spacer 4 may be selected such that sharp images of the biological sample on microscope slide 2 may be obtained by the camera device 8 (or other imaging system component) even if the objective lens 5 has a magnification of 100×.

Figure 33:
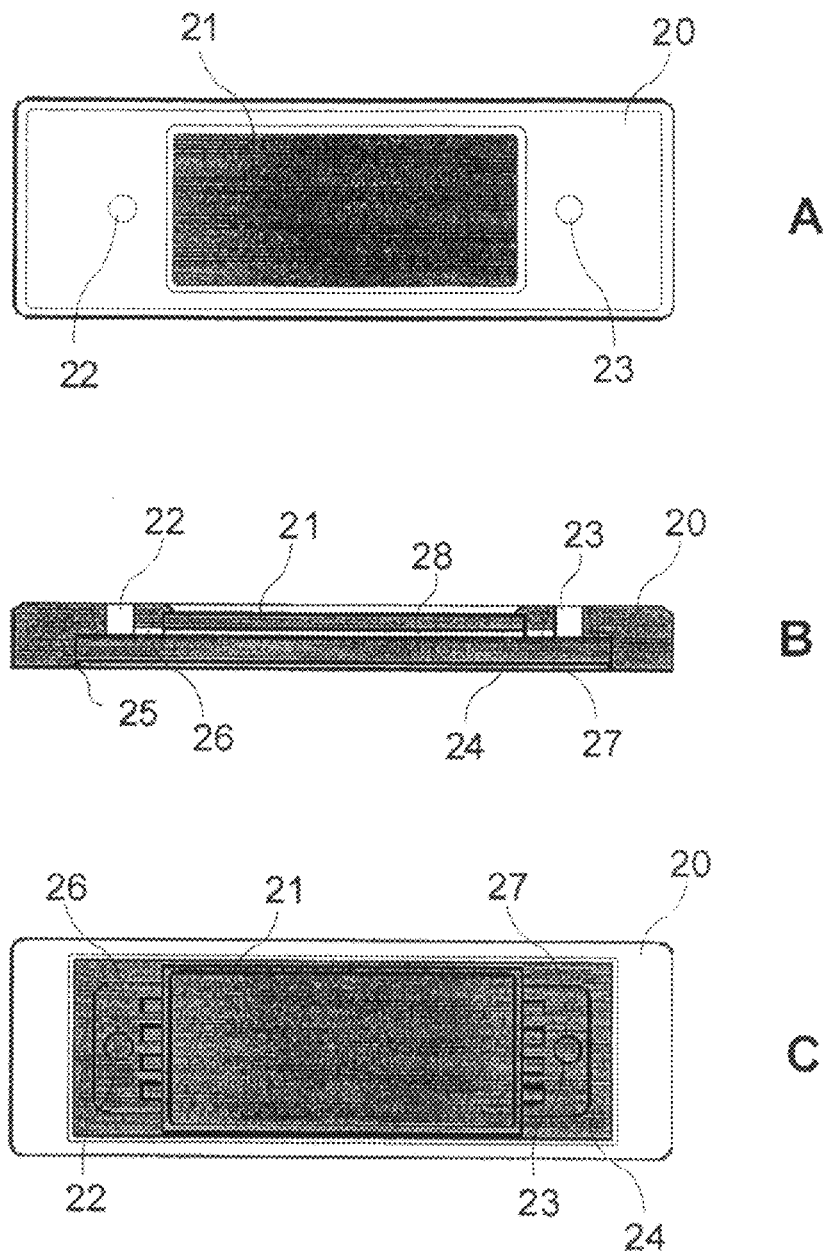
FIG. 33 shows several non-limiting views of a flow chamber, according to one embodiment of the present invention, the flow chamber including a slide defining the surface for operably engaging the sample therewith and a flow channel housing defining a slide aperture configured for receiving the slide.

FIG. 33 shows an example of a snap-in flow-through disposable suitable to practice various method and/or system embodiments of the present invention. FIG. 33A shows the disposable as seen from above, i.e. from where objective lens 5 shown in FIGS. 31 and 32 would be located. In other embodiments, the objective lens 5 may be disposed below the disposable. In such embodiments, FIG. 33A would represent a view from "below". FIG. 33A shows the preformed disposable body 20, which in this example has a cover glass 21 integrated therein. Also shown is a reagent inlet 22 as well as a reagent outlet 23 that may be in fluid communications with the reservoirs 10, 11, 12, 13 shown in FIG. 32, for example). FIG. 33B shows a side view of the disposable depicting a preformed disposable body 20, an integrated cover glass 21, a reagent inlet 22, and a reagent outlet 23. After operably engaging the prepared microscope slide 30 with the body 20, a flow-through chamber 28 with connector channels 26 and 27 to inlet 22 and outlet 23, respectively, is formed. In some embodiments, the disposable body 20 may comprise a corner "lip" feature 25, which may allow the slide 24 to be releasably "snapped-in" to the disposable body to form the flow-through chamber 28 between the slide 30 and body 20. FIG. 33C shows a rear view of the disposable depicting, in particular, one exemplary embodiment of connector channels 26 and 27 that may be defined between the flow-through chamber 28 and at least one of the reagent inlet 22 and the reagent outlet 23.

FIG. 34 illustrates an exemplary procedure for operably engaging a sample 32 with a surface (such as a sample attachment area 31 of a conventional microscope slide 30. In FIG. 34A, the sample 32 to be evaluated may be disposed and thermo-fixed onto an ordinary microscope slide 30 within a typical sample attachment area 31. FIG. 34B is a side view of slide 30 with a sample 32 attached. The prepared slide is then "snapped" into a disposable body with the one side carrying the sample 32 (see FIG. 34C). The disposable body is structured so that the snapped-in microscope slide and a cover glass, (which is integrated into the body) may form a flow channel for the various washing, staining, decolorization, and/or counterstaining reagents that may be used in various embodiments of the present invention. As described herein, the flow chamber may comprise a reagent inlet port and a reagent outlet port for washing reagents into and out of the flow chamber. The completed disposable is shown in FIG. 34D, and is finally turned upside down for positioning on a microscope stage (see FIG. 34E).

FIG. 35 shows a completed disposable, positioned on a microscope and connected with a liquid handling system to perform the various washing (see step 102), staining (see step 104), and/or decolorization (see steps 107 and 112) procedures according to various embodiments of the present invention. In some embodiments, fluid communication between the flow chamber and a liquid handling system (see elements 14, 15 and 16 of FIG. 32, for example) may be established by connector pipes 33 and 34 that may be configured for holding the disposable flow chamber 20 in place relative to the imaging system (and/or an objective lens 5 thereof) and for providing substantially fluid-tight connection to the reagent inlet 22 and the reagent outlet 23 via pressure fittings 35 and 36, respectively. The connector pipes 33, 34 may, in some embodiments, comprise a substantially stiff polymeric substance configured for urging the disposable flow chamber 20 generally downward and into engagement with a stage 1 of the imaging system.

It should be understood that the various system embodiments described herein with respect to FIGS. 31-35 may be configured for performing the various method steps that have been described in connection with the various images shown in FIGS. 1-29 and that are summarized in FIGS. 30 and 36. For example, referring to the system embodiment shown in FIG. 32, the systems controller 19 may be configured for controlling the automated staining process (see step 104, for example) and decolorization processes (see steps 107 and 112). The systems controller 19 may also be configured for communicating with the image processing computer 18 and the actuator device 9 (comprising an XYZ-translation mechanism, for example) to determine when to perform an autofocus operation, when to record an image, when to move to a new field of interest, and when image processing steps (such as image subtraction, for example) should be performed to generate various difference images. In some embodiments, the image processing computer 18 may automatically produce optimized images showing either Gram-positive bacteria or Gram-negative bacteria. Such images may be stored by the image processing computer 18 (in a memory device integrated therein, for example) and made available to a lab technician, microbiologist, or other user so as to enable the user to perform a manual morphology analysis and/or to identify various entities that may be present in a given sample. For example, in some embodiments, the image processing computer 18 may comprise a user interface (such as a high-resolution display (not shown)) configured for generating a visual depiction of the optimized images of Gram-positive bacteria or Gram-negative bacteria within the sample such that a user may perform step 116 for analyzing a morphology of the sample entities without the need to remove the sample from a microscope stage 1 or other analysis field relative to an imaging system. In other embodiments, the image processing computer 18 may comprise a memory device containing an image data base including a variety of known microorganisms (and characteristic stained images corresponding thereto). The image processing computer 18 may then execute an automated bacterial identification procedure, and subsequently offer the result to a user via a user interface. The user may then accept the automated identification output, or use the automated result as a starting point for a follow-up manual confirmation. In these various system embodiments, the sample 32 may remain on the sample stage 1 of the imaging system, so that the user can compare the various difference images generated by the image processing computer 18 with the unprocessed actual image of an optimally-stained sample.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for performing a staining procedure for a biological sample, the method comprising:
    recording a first image of the sample;
    applying a staining agent to the sample so as to prepare a stained sample comprising a plurality of stained entities and/or a plurality of superficially stained entities;
    recording a second image of the stained sample;
    generating a first difference image by comparing the second image to the first image so as to determine a location of at least one of the stained entities on the stained sample, if present;
    applying a decolorizing agent to the stained sample so as to prepare a partially decolorized sample wherein at least a portion of the staining reagent is removed from the superficially stained entities, if present;
    recording a third image of the partially decolorized sample;
    generating a second difference image by comparing the third image to the second image so as to determine a location of at least one of the superficially stained entities on the stained sample, if present; and
    analyzing the second difference image to determine an exposure time during which the decolorizing agent could be applied to the partially decolorized sample to substantially decolorize the superficially stained entities, if present, without substantially decolorizing the stained entities, if present.

2. A method according to claim 1, further comprising applying the decolorizing agent to the partially decolorized sample for the determined exposure time so as to prepare a substantially decolorized sample wherein the superficially stained entities are substantially decolorized, if present, and wherein the stained entities are not substantially decolorized, if present.

3. A method according to claim 2, further comprising:
    recording a fourth image of the substantially decolorized sample;
    generating a third difference image by comparing the fourth image to the second image, the third difference image depicting the location of at least one of the superficially stained entities on the stained sample, if present; and
    generating a fourth difference image by comparing the fourth image to the first image, the fourth difference image depicting a location of at least one of the stained entities on the stained sample, if present.

4. A method according to claim 1, further comprising washing the sample with a washing solution prior to recording the first image of the sample.

5. A method according to claim 3, further comprising analyzing a morphology of the superficially stained entities, if present.

6. A method according to claim 3, further comprising analyzing a morphology of the stained entities, if present.

7. A method according to claim 1, wherein the staining agent comprises a Gram stain and wherein the superficially stained entities comprise a plurality of Gram-negative bacteria, if present, and wherein the stained entities comprise a plurality of Gram-positive bacteria, if present.

8. A system for performing a staining procedure for a biological sample, the system comprising:
    a flow chamber defining channel in fluid communication with a supply of a staining agent and a supply of a decolorizing agent, the flow chamber comprising a surface configured for operably engaging the sample therewith;
    a fluidics system in fluid communication with the flow chamber, the supply of the staining agent, and the supply of the decolorizing agent;
        the fluidics system configured for applying the staining agent to the sample so as to prepare a stained sample comprising a plurality of stained entities and/or a plurality of superficially stained entities;
        the fluidics system further configured for applying the decolorizing agent to the stained sample so as to prepare a partially decolorized sample wherein at least a portion of the stain is removed from the stained sample;
    an imaging system disposed adjacent to the flow chamber and configured for recording at least one image of the sample before, during, and/or after the application of the staining agent and the decolorizing agent; and a controller device in communication with the imaging system and the fluidics system, the controller device being configured to control the application of at least one of the staining agent and the decolorizing agent based at least in part on the at least one image, wherein the imaging system is further configured to determine an exposure time for an application of the decolorizing agent.

9. A system according to claim 8, wherein the imaging system is configured for recording a first image of the sample;
the imaging system further configured for recording a second image of the stained sample after applying the staining agent to the sample using the fluidics system;
the imaging system further configured for generating a first difference image by comparing the second image to the first image so as to determine a location of at least one of the stained entities on the stained sample, if present;
the imaging system further configured for recording a third image of the partially decolorized sample after applying the decolorizing agent using the fluidics system;
the imaging system further configured for generating a second difference image by comparing the third image to the second image so as to determine a location of at least one of the superficially stained entities, if present; and
the imaging system further configured for analyzing the second difference image to determine an exposure time during which the decolorizing agent could be applied to the partially decolorized sample to substantially decolorize the superficially stained entities, if present, without substantially decolorizing the stained entities, if present.

10. A system according to claim 8, wherein the flow chamber is adapted for receiving a slide defining the surface for operably engaging the sample therewith and wherein the flow chamber comprises a flow channel housing defining a slide aperture configured for receiving the slide such that the sample is disposed substantially between the slide and the flow channel housing when the slide is disposed in the slide aperture, the flow channel housing comprising a substantially translucent material such that the imaging system is capable of recording the at least one image of the sample while the sample is disposed between the slide and the flow channel housing.

11. A system according to claim 8, wherein the imaging system comprises:
a camera device configured for recording the at least one image of the sample while the sample is disposed between the slide and the flow channel housing; and
an actuator device operably engaged with the camera device and configured for adjusting a position of the camera device relative to the flow chamber.

12. A system according to claim 8, wherein the fluidics system is further configured for cooperating with the flow chamber for applying the decolorizing agent to the partially decolorized sample for the determined exposure time so as to prepare a substantially decolorized sample wherein the superficially stained entities are substantially decolorized if present, and wherein the stained entities are not substantially decolorized if present.

13. A system according to claim 9, wherein the imaging system is further configured for:
recording a fourth image of the substantially decolorized sample;
generating a third difference image by comparing the fourth image to the second image, the third difference image depicting the location of at least one of the superficially stained entities, if present; and
generating a fourth difference image by comparing the fourth image to the first image, the fourth difference depicting a location of at least one of the stained entities, if present.

14. A system according to claim 9, wherein the imaging system comprises an image processing computer configured for analyzing the second difference image.

15. A system according to claim 14, wherein the imaging system comprises an image processing computer configured for generating at least one of the first difference image, the second difference image, the third difference image, and the fourth difference image.

16. A system according to claim 15, wherein the image processing computer is configured for generating at least one of the first difference image, the second difference image, the third difference image, and the fourth difference image using processes selected from the group consisting of:
image subtraction;
image addition;
image ratio calculation; and
combinations thereof.

17. A system according to claim 8, wherein the staining agent comprises a Gram stain and wherein the superficially stained entities comprise a plurality of Gram-negative bacteria, if present, and wherein the stained entities comprise a plurality of Gram-positive bacteria, if present.

18. A system for performing a staining procedure for a biological sample, the system comprising:
a flow chamber defining a channel in fluid communication with a supply of a staining agent and a supply of a decolorizing agent, the flow chamber comprising a surface configured for operably engaging the sample therewith;
a fluidics system in fluid communication with the flow chamber, the supply of the staining agent, and the supply of the decolorizing agent;
the fluidics system configured for applying the staining agent to the sample so as to prepare a stained sample comprising a plurality of stained entities and/or a plurality of superficially stained entities;
the fluidics system further configured for applying the decolorizing agent to the stained sample so as to prepare a partially decolorized sample wherein at least a portion of the stain is removed from the stained sample; and
an imaging system disposed adjacent to the flow chamber such that the sample is positioned within a field of view of the imaging system;
the imaging system configured for monitoring an application of at least one of the staining agent and the decolorizing agent;
the imaging system further configured for generating a difference image by comparing at least one image of the sample obtained before a first application of the decolorizing agent and at least one image of the sample obtained after the first application of the decolorizing agent;
the imaging system being further configured to determine an exposure time for a second application of the decolorizing agent based at least in part on the difference image so as to substantially decolorize the superficially stained entities, if present, without substantially decolorizing the stained entities, if present, such that the stained entities may be more readily discerned from the superficially stained entities.

19. A system according to claim 18, wherein the flow chamber is adapted for receiving a slide defining the surface for operably engaging the sample therewith and wherein the flow chamber comprises a flow channel housing defining a slide aperture configured for receiving the slide such that the sample is disposed substantially between the slide and the flow channel housing when the slide is disposed in the slide aperture, the flow channel housing comprising a substantially translucent material such that the imaging system is capable of recording images of the sample while the sample is disposed between the slide and the flow channel housing.

20. A system according to claim 18, wherein the imaging system comprises:
   a camera device configured to be capable of recording images of the sample while the sample is disposed between the slide and the flow channel housing; and
   an actuator device operably engaged with the camera device and configured for adjusting a position of the camera device relative to the flow chamber.

21. A system according to claim 18, wherein the imaging system comprises an image processing computer configured for generating the difference image.

22. A system according to claim 18, wherein the image processing computer is configured for generating the difference image using processes selected from the group consisting of:
   image subtraction;
   image addition;
   image ratio calculation; and
   combinations thereof 23. A system according to claim 18, wherein the staining agent comprises a Gram stain and wherein the superficially stained entities comprise a plurality of Gram-negative bacteria, if present, and wherein the stained entities comprise a plurality of Gram-positive bacteria, if present.

24. A method for optimally staining a biological sample, the method comprising:
   operably engaging a sample with a sample stage of an imaging system;
   recording images of the sample using the imaging system before and after an application of a staining agent and a decolorization agent to the sample;
   generating a difference image based at least in part on a comparison of the images of the sample recorded before and after the application of the staining agent and the decolorization agent to the sample;
   correcting the application of at least one of the staining agent and the decolorization agent based at least in part on the difference image;
   reapplying at least one of the staining agent and the decolorization agent according to the correcting step; and
   generating a final image of the sample so as to differentiate at least one target of interest in the sample that is rendered discernible by the reapplying step.

25. A method according to claim 24, wherein the staining agent comprises a Gram stain and wherein the application of the staining reagent to the sample is configured for indicating the presence of a plurality of superficially stained entities comprising a plurality of Gram-negative bacteria, if present, and the presence of a plurality of stained entities comprising a plurality of Gram-positive bacteria, if present.

26. A method for optimally staining a biological sample, the method comprising:
   applying a staining agent to a sample to prepare a stained sample comprising a plurality of stained entities and/or a plurality of superficially stained entities;
   applying a decolorization agent to the sample so as to prepare a partially decolorized sample wherein at least a portion of the staining agent is removed from the stained sample;
   recording at least one image of the sample before and after an application of the staining agent and after application of the decolorization agent to the sample;
   generating at least one difference image based at least in part on a comparison of the images of the sample recorded before and after the application of the staining agent and after the application of the decolorization agent to the sample; and
   correcting the application of the staining agent and/or the decolorization agent based at least in part on the at least one difference image.

27. A system for performing a staining procedure for a biological sample, the system comprising:
   a flow chamber defining channel in fluid communication with a supply of a staining agent and a supply of a decolorizing agent, the flow chamber comprising a surface configured for operably engaging the sample therewith;
   a fluidics system in fluid communication with the flow chamber, the supply of the staining agent, and the supply of the decolorizing agent;
      the fluidics system configured for applying the staining agent to the sample so as to prepare a stained sample comprising a plurality of stained entities and/or a plurality of superficially stained entities;
      the fluidics system further configured for applying the decolorizing agent to the stained sample so as to prepare a partially decolorized sample wherein at least a portion of the stain is removed from the stained sample;
   an imaging system disposed adjacent to the flow chamber and configured for recording at least one image of the sample before, during, and/or after the application of the staining agent and the decolorizing agent, the imaging system further configured to generate at least one difference image based at least in part on a comparison of images of the sample recorded before and after the application of the staining agent and after the application of the decolorization agent to the sample; and
   a controller device in communication with the imaging system and the fluidics system, the controller device being configured to control the application of the staining agent and/or the decolorizing agent based at least in part on the at least one difference image.

* * * * *

UNITED STATES PATENT AND TRADEMARK OFFICE
CERTIFICATE OF CORRECTION

PATENT NO.       : 8,600,142 B2                                         Page 1 of 1
APPLICATION NO.  : 12/529065
DATED            : December 3, 2013
INVENTOR(S)      : Klaus W. Berndt It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1079 days.

Signed and Sealed this
Twenty-second Day of September, 2015

Michelle K. Lee
*Director of the United States Patent and Trademark Office*